United States Patent
Hauck et al.

(10) Patent No.: US 9,204,935 B2
(45) Date of Patent: *Dec. 8, 2015

(54) ROBOTIC SURGICAL SYSTEM AND METHOD FOR DIAGNOSTIC DATA MAPPING

(71) Applicant: St. Jude Medical, Atrial Fibrillation Division, Inc., St. Paul, MN (US)

(72) Inventors: John A. Hauck, Shoreview, MN (US); Jeffrey A. Schweitzer, St. Paul, MN (US); Kedar Ravindra Belhe, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/306,972

(22) Filed: Jun. 17, 2014

(65) Prior Publication Data

US 2014/0371576 A1 Dec. 18, 2014

Related U.S. Application Data

(63) Continuation of application No. 11/647,298, filed on Dec. 29, 2006, now Pat. No. 8,755,864, and a continuation-in-part of application No. 11/139,908, filed on May 27, 2005, now Pat. No. 7,632,265.

(60) Provisional application No. 60/851,042, filed on Oct. 12, 2006, provisional application No. 60/575,741, filed on May 28, 2004.

(51) Int. Cl.
*A61B 5/05* (2006.01)
*A61B 5/06* (2006.01)
(Continued)

(52) U.S. Cl.
CPC ......... *A61B 19/2203* (2013.01); *A61B 5/04011* (2013.01); *A61B 5/06* (2013.01);
(Continued)

(58) Field of Classification Search
None
See application file for complete search history.

(56) References Cited

U.S. PATENT DOCUMENTS 4,170,876 A   10/1979   Dits et al.
4,510,574 A    4/1985   Guittet et al.
(Continued)

FOREIGN PATENT DOCUMENTS

EP    1779802      5/2007
WO    9744089     11/1997
(Continued)

OTHER PUBLICATIONS

Extended European Search Report for EP 08798257.5 dated Aug. 17, 2011.
(Continued)

*Primary Examiner* — Carl H Layno
*Assistant Examiner* — Jon Eric C Morales
(74) *Attorney, Agent, or Firm* — Wiley Rein LLP

(57) ABSTRACT

A method of generating a diagnosis map of at least a portion of the heart includes inserting an electrode within the portion of a heart, robotically moving the electrode therein, measuring electrophysiology information at a point on the surface of the heart, associating the measured electrophysiology information with position information for the point on the surface of the heart, repeating the measuring and associating steps for a plurality of points on the surface of the heart, thereby generating a plurality of surface diagnostic data points, and generating the diagnosis map therefrom. The electrode may be moved within the heart randomly, pseudo-randomly, or according to one or more predetermined patterns. A three-dimensional model of the portion of the heart may be provided and presented as a graphical representation, either with or without information indicative of the measured electrophysiology information superimposed thereon.

14 Claims, 19 Drawing Sheets

(51) Int. Cl.
*A61B 19/00* (2006.01)
*A61B 5/00* (2006.01)
*A61B 5/04* (2006.01)
*A61B 17/00* (2006.01)
*A61M 25/01* (2006.01)

(52) U.S. Cl.
CPC ............ *A61B 5/6885* (2013.01); *A61B 5/7425* (2013.01); *A61B 5/7475* (2013.01); *A61B 19/5244* (2013.01); *A61B 2017/00026* (2013.01); *A61B 2019/2211* (2013.01); *A61B 2019/2219* (2013.01); *A61B 2019/2242* (2013.01); *A61B 2019/2276* (2013.01); *A61B 2019/464* (2013.01); *A61B 2019/505* (2013.01); *A61B 2019/528* (2013.01); *A61B 2019/5251* (2013.01); *A61B 2019/5253* (2013.01); *A61B 2019/5272* (2013.01); *A61M 25/0105* (2013.01)

(56) References Cited

U.S. PATENT DOCUMENTS

| | | |
|---|---|---|
| 4,710,876 A | 12/1987 | Cline et al. |
| 4,721,114 A | 1/1988 | DuFault et al. |
| 4,785,399 A | 11/1988 | Evans et al. |
| 4,837,734 A | 6/1989 | Ichikawa et al. |
| 4,854,324 A | 8/1989 | Hirschman et al. |
| 4,873,572 A | 10/1989 | Miyazaki et al. |
| 4,921,482 A | 5/1990 | Hammerslag et al. |
| 5,078,140 A | 1/1992 | Kwoh |
| 5,114,414 A | 5/1992 | Buchbinder |
| 5,199,950 A | 4/1993 | Schmitt et al. |
| 5,222,501 A | 6/1993 | Ideker et al. |
| RE34,502 E | 1/1994 | Webster |
| 5,275,164 A | 1/1994 | Maeda et al. |
| 5,281,220 A | 1/1994 | Blake, III |
| 5,339,799 A | 8/1994 | Kami et al. |
| 5,368,564 A | 11/1994 | Savage |
| 5,385,148 A | 1/1995 | Lesh et al. |
| 5,389,073 A | 2/1995 | Imran |
| 5,391,147 A | 2/1995 | Imran et al. |
| 5,391,199 A | 2/1995 | Ben-Haim |
| 5,396,887 A | 3/1995 | Imran |
| 5,400,783 A | 3/1995 | Pomeranz et al. |
| 5,404,638 A | 4/1995 | Imran |
| 5,406,946 A | 4/1995 | Imran |
| 5,409,000 A | 4/1995 | Imran |
| 5,415,166 A | 5/1995 | Imran |
| 5,423,811 A | 6/1995 | Imran et al. |
| 5,425,364 A | 6/1995 | Imran |
| 5,425,375 A | 6/1995 | Chin et al. |
| 5,431,645 A | 7/1995 | Smith et al. |
| 5,465,717 A | 11/1995 | Imran et al. |
| 5,476,100 A | 12/1995 | Galel |
| 5,478,330 A | 12/1995 | Imran et al. |
| 5,492,131 A | 2/1996 | Galel |
| 5,496,311 A | 3/1996 | Abele et al. |
| 5,498,239 A | 3/1996 | Galel et al. |
| 5,507,802 A | 4/1996 | Imran |
| 5,527,279 A | 6/1996 | Imran |
| 5,533,967 A | 7/1996 | Imran |
| 5,545,161 A | 8/1996 | Imran |
| 5,555,897 A | 9/1996 | Lathrop, Jr. et al. |
| 5,558,073 A | 9/1996 | Pomeranz et al. |
| 5,578,007 A | 11/1996 | Imran |
| 5,588,964 A | 12/1996 | Imran et al. |
| 5,607,462 A | 3/1997 | Imran |
| 5,632,734 A | 5/1997 | Galel et al. |
| 5,656,029 A | 8/1997 | Imran et al. |
| 5,658,278 A | 8/1997 | Imran et al. |
| 5,662,108 A | 9/1997 | Budd et al. |
| 5,673,704 A | 10/1997 | Marchlinski et al. |
| 5,680,860 A | 10/1997 | Imran |
| 5,681,280 A | 10/1997 | Rusk et al. |
| 5,697,377 A | 12/1997 | Wittkampf |
| 5,697,927 A | 12/1997 | Imran et al. |
| 5,722,401 A | 3/1998 | Pietroski et al. |
| 5,730,128 A | 3/1998 | Pomeranz et al. |
| 5,754,741 A | 5/1998 | Wang et al. |
| 5,782,899 A | 7/1998 | Imran |
| RE35,880 E | 8/1998 | Waldman et al. |
| 5,800,482 A | 9/1998 | Pomeranz et al. |
| 5,808,665 A | 9/1998 | Green |
| 5,813,991 A | 9/1998 | Willis et al. |
| 5,820,568 A | 10/1998 | Willis |
| 5,823,199 A | 10/1998 | Hastings et al. |
| 5,835,458 A | 11/1998 | Bischel et al. |
| 5,861,024 A | 1/1999 | Rashidi |
| 5,876,325 A | 3/1999 | Mizuno et al. |
| 5,882,333 A | 3/1999 | Schaer et al. |
| 5,882,346 A | 3/1999 | Pomeranz et al. |
| 5,895,417 A | 4/1999 | Pomeranz et al. |
| 5,906,605 A | 5/1999 | Coxum |
| 5,908,446 A | 6/1999 | Imran |
| 5,940,240 A | 8/1999 | Kupferman |
| 5,954,665 A | 9/1999 | Ben-Haim |
| 5,964,732 A | 10/1999 | Willard |
| 5,964,796 A | 10/1999 | Imran |
| 5,971,967 A | 10/1999 | Willard |
| 5,983,126 A | 11/1999 | Wittkampf |
| 5,993,462 A | 11/1999 | Pomeranz et al. |
| 5,997,532 A | 12/1999 | McLaughlin et al. |
| 6,004,271 A | 12/1999 | Moore |
| 6,010,500 A | 1/2000 | Sherman et al. |
| 6,014,579 A | 1/2000 | Pomeranz et al. |
| 6,015,407 A | 1/2000 | Rieb et al. |
| 6,032,077 A | 2/2000 | Pomeranz |
| 6,049,732 A | 4/2000 | Panescu et al. |
| 6,063,022 A | 5/2000 | Ben-Haim |
| 6,066,125 A | 5/2000 | Webster |
| 6,075,871 A | 6/2000 | Simanovsky et al. |
| 6,083,170 A | 7/2000 | Ben-Haim |
| 6,089,235 A | 7/2000 | Hastings et al. |
| 6,096,004 A | 8/2000 | Meglan et al. |
| 6,119,041 A | 9/2000 | Pomeranz et al. |
| 6,123,699 A | 9/2000 | Webster |
| 6,197,017 B1 | 3/2001 | Brock et al. |
| 6,210,362 B1 | 4/2001 | Ponzi |
| 6,216,027 B1 | 4/2001 | Willis et al. |
| 6,221,060 B1 | 4/2001 | Willard |
| 6,227,077 B1 | 5/2001 | Chiang |
| 6,235,022 B1 | 5/2001 | Hallock et al. |
| 6,236,883 B1 | 5/2001 | Ciaccio et al. |
| 6,241,666 B1 | 6/2001 | Pomeranz et al. |
| 6,258,060 B1 | 7/2001 | Willard |
| 6,272,371 B1 | 8/2001 | Shlomo |
| 6,277,077 B1 | 8/2001 | Brisken et al. |
| 6,285,898 B1 | 9/2001 | Ben-Haim |
| 6,289,239 B1 | 9/2001 | Panescu et al. |
| 6,292,681 B1 | 9/2001 | Moore |
| 6,298,257 B1 | 10/2001 | Hall et al. |
| 6,375,471 B1 | 4/2002 | Wendlandt et al. |
| 6,398,755 B1 | 6/2002 | Belef et al. |
| 6,432,112 B2 | 8/2002 | Brock et al. |
| 6,436,107 B1 | 8/2002 | Wang et al. |
| 6,451,027 B1 | 9/2002 | Cooper et al. |
| 6,490,474 B1 | 12/2002 | Willis et al. |
| 6,493,608 B1 | 12/2002 | Niemeyer |
| 6,500,167 B1 | 12/2002 | Webster |
| 6,516,211 B1 | 2/2003 | Acker et al. |
| 6,517,477 B1 | 2/2003 | Wendlandt |
| 6,554,820 B1 | 4/2003 | Wendlandt et al. |
| 6,554,844 B2 | 4/2003 | Lee et al. |
| 6,569,160 B1 | 5/2003 | Goldin et al. |
| 6,572,554 B2 | 6/2003 | Yock |
| 6,596,084 B1 | 7/2003 | Patke |
| 6,620,202 B2 | 9/2003 | Bottcher et al. |
| 6,640,119 B1 | 10/2003 | Budd et al. |
| 6,650,920 B2 | 11/2003 | Schaldach et al. |
| 6,658,279 B2 | 12/2003 | Swanson et al. |
| 6,659,956 B2 | 12/2003 | Barzell et al. |
| 6,663,622 B1 | 12/2003 | Foley et al. |
| 6,679,269 B2 | 1/2004 | Swanson |
| 6,679,836 B2 | 1/2004 | Couvillon |

(56) References Cited

U.S. PATENT DOCUMENTS

| | | |
|---|---|---|
| 6,692,485 B1 | 2/2004 | Brock et al. |
| 6,695,785 B2 | 2/2004 | Brisken et al. |
| 6,699,179 B2 | 3/2004 | Wendlandt |
| 6,716,190 B1 | 4/2004 | Glines et al. |
| 6,718,196 B1 | 4/2004 | Mah et al. |
| 6,719,804 B2 | 4/2004 | St. Pierre |
| 6,726,675 B1 | 4/2004 | Beyar |
| 6,728,562 B1 | 4/2004 | Budd et al. |
| 6,731,976 B2 | 5/2004 | Penn et al. |
| 6,752,800 B1 | 6/2004 | Winston et al. |
| 6,754,450 B2 | 6/2004 | Chang et al. |
| 6,764,450 B2 | 7/2004 | Yock |
| 6,770,027 B2 | 8/2004 | Banik et al. |
| 6,783,521 B2 | 8/2004 | Ponzi et al. |
| 6,810,281 B2 | 10/2004 | Brock et al. |
| 6,817,974 B2 | 11/2004 | Cooper et al. |
| 6,835,173 B2 | 12/2004 | Couvillon et al. |
| 6,837,867 B2 | 1/2005 | Kortelling |
| 6,843,793 B2 | 1/2005 | Brock et al. |
| 6,858,003 B2 | 2/2005 | Evans et al. |
| 6,860,878 B2 | 3/2005 | Brock |
| 6,872,178 B2 | 3/2005 | Weinberg |
| 6,874,789 B2 | 4/2005 | Shedlov |
| 6,892,091 B1 | 5/2005 | Ben-Haim et al. |
| 6,913,594 B2 | 7/2005 | Coleman et al. |
| 6,926,669 B1 | 8/2005 | Stewart et al. |
| 6,939,309 B1 | 9/2005 | Beatty et al. |
| 6,946,092 B1 | 9/2005 | Bertolino et al. |
| 6,947,785 B1 | 9/2005 | Beatty et al. |
| 6,949,106 B2 | 9/2005 | Brock et al. |
| 6,955,674 B2 | 10/2005 | Eick et al. |
| 6,962,669 B2 | 11/2005 | Foreman et al. |
| 6,974,455 B2 | 12/2005 | Garabedian et al. |
| 6,974,465 B2 | 12/2005 | Belef et al. |
| 6,978,168 B2 | 12/2005 | Beatty et al. |
| 6,990,370 B1 | 1/2006 | Beatty et al. |
| 6,997,870 B2 | 2/2006 | Couvillon |
| 7,022,077 B2 | 4/2006 | Mourad et al. |
| 7,025,064 B2 | 4/2006 | Wang et al. |
| 7,027,892 B2 | 4/2006 | Wang et al. |
| 7,037,345 B2 | 5/2006 | Bottcher et al. |
| 7,076,300 B1 | 7/2006 | Kroll et al. |
| 7,189,208 B1 | 3/2007 | Beatty et al. |
| 7,344,533 B2 | 3/2008 | Pearson et al. |
| 7,479,106 B2 | 1/2009 | Banik et al. |
| 7,632,265 B2 | 12/2009 | Hauck et al. |
| 7,806,829 B2 | 10/2010 | Hauck |
| 8,755,864 B2 * | 6/2014 | Hauck et al. ............... 600/424 |
| 2001/0027316 A1 | 10/2001 | Gregory |
| 2002/0042570 A1 | 4/2002 | Schaldach et al. |
| 2002/0045809 A1 | 4/2002 | Ben-Haim |
| 2002/0087166 A1 | 7/2002 | Brock et al. |
| 2002/0087169 A1 | 7/2002 | Brock et al. |
| 2002/0120188 A1 | 8/2002 | Brock et al. |
| 2002/0123749 A1 | 9/2002 | Jain |
| 2002/0128633 A1 | 9/2002 | Brock et al. |
| 2002/0143319 A1 | 10/2002 | Brock |
| 2002/0143326 A1 | 10/2002 | Foley et al. |
| 2002/0177789 A1 | 11/2002 | Ferry et al. |
| 2003/0036696 A1 | 2/2003 | Willis et al. |
| 2003/0055410 A1 | 3/2003 | Evans et al. |
| 2003/0199904 A1 | 10/2003 | Boecker et al. |
| 2004/0049205 A1 | 3/2004 | Lee et al. |
| 2004/0059237 A1 | 3/2004 | Narayan et al. |
| 2004/0073206 A1 | 4/2004 | Foley et al. |
| 2004/0098075 A1 | 5/2004 | Lee |
| 2004/0128026 A1 | 7/2004 | Harris et al. |
| 2004/0176751 A1 | 9/2004 | Weitzner et al. |
| 2004/0193146 A1 | 9/2004 | Lee et al. |
| 2005/0004579 A1 | 1/2005 | Sneider et al. |
| 2005/0049580 A1 | 3/2005 | Brock et al. |
| 2005/0096643 A1 | 5/2005 | Brucker et al. |
| 2005/0102017 A1 | 5/2005 | Mattison |
| 2005/0137478 A1 | 6/2005 | Younge et al. |
| 2005/0192488 A1 | 9/2005 | Bryenton et al. |
| 2005/0197530 A1 | 9/2005 | Wallace et al. |
| 2005/0203382 A1 * | 9/2005 | Govari et al. ............... 600/424 |
| 2005/0203394 A1 | 9/2005 | Hauck |
| 2005/0209589 A1 | 9/2005 | Berman et al. |
| 2005/0215983 A1 | 9/2005 | Brock |
| 2005/0216033 A1 | 9/2005 | Lee |
| 2005/0222554 A1 * | 10/2005 | Wallace et al. ............... 606/1 |
| 2005/0228440 A1 | 10/2005 | Brock et al. |
| 2005/0234437 A1 | 10/2005 | Baxter et al. |
| 2006/0004352 A1 | 1/2006 | Vaska et al. |
| 2006/0015096 A1 | 1/2006 | Hauck et al. |
| 2006/0052695 A1 | 3/2006 | Adam |
| 2006/0057560 A1 | 3/2006 | Hlavkak et al. |
| 2006/0058692 A1 | 3/2006 | Beatty et al. |
| 2006/0084945 A1 | 4/2006 | Moll et al. |
| 2006/0084960 A1 | 4/2006 | Mester et al. |
| 2006/0095022 A1 | 5/2006 | Moll et al. |
| 2006/0098010 A1 | 5/2006 | Dwyer et al. |
| 2006/0100610 A1 | 5/2006 | Wallace et al. |
| 2006/0111692 A1 | 5/2006 | Hlavka et al. |
| 2006/0116575 A1 | 6/2006 | Willis |
| 2006/0149139 A1 | 7/2006 | Bonmassar et al. |
| 2006/0258935 A1 | 11/2006 | Pile-Spellman |
| 2007/0021679 A1 | 1/2007 | Narayan et al. |
| 2007/0043296 A1 | 2/2007 | Schwartz |
| 2007/0057945 A1 | 3/2007 | Olson |
| 2007/0060833 A1 | 3/2007 | Hauck |
| 2007/0073179 A1 | 3/2007 | Afonso et al. |
| 2007/0185485 A1 | 8/2007 | Hauck et al. |
| 2007/0197896 A1 | 8/2007 | Moll et al. |
| 2007/0208260 A1 | 9/2007 | Afonso |
| 2008/0015670 A1 | 1/2008 | Pappone |
| 2009/0105579 A1 | 4/2009 | Garibaldi |

FOREIGN PATENT DOCUMENTS

| | | |
|---|---|---|
| WO | 0007501 | 2/2000 |
| WO | 0007503 | 2/2000 |
| WO | 0125822 | 4/2001 |
| WO | 2004047632 | 6/2004 |
| WO | 2005042053 | 5/2005 |
| WO | 2005044081 | 5/2005 |
| WO | 2005112750 | 12/2005 |
| WO | 2005117596 | 12/2005 |
| WO | 2006059089 | 6/2006 |
| WO | 2007005976 | 1/2007 |

OTHER PUBLICATIONS

International Search Report and Written Opinion dated Nov. 13, 2008 for PCT/US08/073694.

International Search Report and Written Opinion dated Jun. 23, 2008 for PCT/US07/080706.

International Search Report and Written Opinion dated May 13, 2008 for PCT/US07/080698.

International Search Report and Written Opinion dated Apr. 16, 2008 for PCT/US07/080705.

International Search Report and Written Opinion dated Apr. 15, 2008 for PCT/US07/080701.

International Search Report and Written Opinion dated Apr. 16, 2008 for PCT/US07/080702.

International Search Report and Written Opinion dated Apr. 16, 2008 for PCT/US07/080703.

* cited by examiner

US 9,204,935 B2

ROBOTIC SURGICAL SYSTEM AND METHOD FOR DIAGNOSTIC DATA MAPPING

CROSS-REFERENCE TO RELATED APPLICATIONS

This application is a continuation of U.S. patent application Ser. No. 11/647,298, filed 29 Dec. 2006 (the '298 application), now U.S. Pat. No. 8,755,864, which claims the benefit of U.S. provisional application No. 60/851,042, filed 12 Oct. 2006 (the '042 application), both of which are hereby incorporated by reference as though fully set forth herein. The '298 application is also a continuation-in-part of U.S. application Ser. No. 11/139,908, filed 27 May 2005 (the '908 application), now pending, which claims the benefit of U.S. provisional application No. 60/575,741, filed 28 May 2004 (the '741 application). The '908 and '741 applications are hereby incorporated by reference as though fully set forth herein.

BACKGROUND OF THE INVENTION a. Field of the Invention

The instant invention relates to robotically controlled medical devices. In particular, the instant invention relates to a robotic surgical system for navigating a medical device through a patient's body for diagnostic and therapeutic purposes.

b. Background Art

Catheters are used for an ever growing number of medical procedures. To name just a few examples, catheters are used for diagnostic, therapeutic, and ablation procedures. Typically, the user manually manipulates the catheter through the patient's vasculature to the intended site, such as a site within the patient's heart. The catheter typically carries one or more electrodes or other diagnostic or therapeutic devices, which may be used for ablation, diagnosis, cardiac mapping, or the like.

It is well known that, to facilitate manipulation of the catheter through the patient's vasculature to the intended site, portions of the catheter shaft, especially the distal regions thereof, may be made steerable. For example, the catheter may be manufactured such that the user can translate, rotate, and deflect the distal end of the catheter as necessary and desired to negotiate the tortuous paths of the patient's vasculature en route to the target site. Navigating a catheter reliably through the patient's body to a precise location, however, is an extremely tedious process requiring a substantial amount of time and skill and potentially causing a high degree of fatigue in the physician, especially where actuation forces are transmitted over large distances.

BRIEF SUMMARY OF THE INVENTION

It is thus desirable to be able to navigate a medical device accurately and precisely through a patient's body to the locations of diagnostic or therapeutic interest.

It is also desirable to be able to reduce the fatigue factor associated with navigating a medical device through a patient's body.

It is further desirable to be able to preserve the ability to manually navigate a medical device when so desired.

It is also desirable that the medical device be able to distinguish proximity or degree of contact between the medical device and a tissue surface.

It is further desirable that the medical device be usable to create a map of a geometry of the patient's body, which map may include diagnostic information, without the need to distinguish surface points from interior points during the data-gathering phase.

According to a first embodiment of the invention, a system for generating a diagnosis map of at least a portion of a heart includes: a catheter for insertion into an interior region of the heart; a controller for moving the catheter within the heart; a position detector to detect position information of the catheter and to generate position information for a point on a surface of the heart that is in meaningful proximity to the catheter; an instrument to measure electrophysiology information at the point on the surface of the heart; and a processor to cause the controller to move the catheter into meaningful proximity with a plurality of points on the surface of the heart, to detect position information for each of the plurality of points on the surface of the heart, to associate the electrophysiology information with one of the plurality of points on the surface of the heart at which the electrophysiology information was measured, and to generate the diagnosis map of the portion of the heart. Optionally, the system includes a storage medium for storing the diagnosis map. The system may also include a three-dimensional surface model of the portion of the heart, and a display device may be provided for presenting a graphical representation of the three-dimensional surface model of the portion of the heart. Optionally, the system further includes: an electrophysiology processor for processing the measured electrophysiology information to identify one or more points on the surface of the heart that are potential treatment sites, the processor being coupled to the display device so that the one or more identified potential treatment sites may be superimposed on the graphical representation of the three-dimensional model and displayed on the display device; and an interface to permit a user to select one or more of the identified potential treatment sites, the interface being coupled to the controller and to the catheter such that the controller may cause the catheter to be relocated to the one or more selected treatment sites.

In another aspect of the present invention, a method of generating a diagnosis map of at least a portion of a heart includes the steps of: inserting an electrode within a portion of a heart; robotically moving the electrode within the portion of the heart; measuring electrophysiology information at a point on the surface of the heart in meaningful proximity to the electrode; associating the measured electrophysiology information with position information for the point on the surface of the heart; repeating the measuring and associating steps for a plurality of points on the surface of the heart, thereby generating a plurality of surface diagnostic data points; and generating the diagnosis map from the plurality of surface diagnostic data points. The step of robotically moving the electrode within the portion of the heart may include moving the electrode randomly within the portion of the heart. Optionally, the method includes storing the plurality of surface diagnostic data points or providing a three-dimensional model of the portion of the heart. The model may be presented as a graphical representation with information indicative of the measured electrophysiology information superimposed thereon.

In yet another aspect of the present invention, a method of generating a diagnosis map of at least a portion of a heart includes the steps of: inserting an electrode within a portion of a heart; robotically moving the electrode within the portion of the heart; detecting position information of the electrode, thereby generating a plurality of location points that define a space occupied by the portion of the heart; measuring electrophysiology information at a plurality of surface points where the electrode is in meaningful proximity to a surface of the heart; associating the measured electrophysiology information with the surface point at which the measurement was made; storing the measured electrophysiology information and location information for the contact point at which the measurement was made; and generating a three-dimensional model of the portion of the heart comprising location information and associated electrophysiology information for at least some of the plurality of surface points. Optionally, the method also includes the steps of: presenting a graphical representation of the three-dimensional model of the portion of the heart; receiving input that identifies one or more target locations on the graphical representation of the three-dimensional model of the portion of the heart; and robotically moving the electrode to each of the identified target locations. The method may also include presenting the graphical representation of the three-dimensional model of the portion of the heart with information indicative of the measured electrophysiology information superimposed thereon. If desired, tissue may be treated, for example ablated, at each of the identified target locations. Alternatively, the method may include: presenting a graphical representation of the three-dimensional model of the portion of the heart; processing the measured electrophysiology information to identify one or more contact points that are potential treatment sites; and flagging the one or more identified potential treatment sites on the graphical representation of the three-dimensional model of the portion of the heart. Optionally, the method includes receiving input that selects one or more of the identified potential treatments sites and robotically moving the electrode to the at least one selected treatment site. Tissue may be treated, for example ablated, at the at least one selected treatment site.

In yet another aspect of the present invention, a method of generating a diagnosis map of at least a portion of a heart includes the steps of: inserting an electrode within a portion of a heart; using a robotic controller to move the electrode within the portion of the heart; detecting position information of the electrode, thereby generating a plurality of location points that define a space occupied by the portion of the heart; processing the plurality of location points to distinguish those location points that are interior to a surface of the portion of the heart; generating a plurality of surface points defining a three-dimensional surface model of the portion of the heart; measuring electrophysiology information of at least some of the plurality of surface points; associating measured electrophysiology information with the surface point at which the measurement was made; and storing the plurality of surface points defining the three-dimensional surface model of the portion of the heart with the associated measured electrophysiology information. Optionally, the method further includes: presenting a graphical representation of the three-dimensional surface model of the portion of the heart; receiving input that identifies one or more target locations on the graphical representation; and robotically moving the electrode to each of the identified target locations. The method may also include the steps of: presenting a graphical representation of the three-dimensional surface model of the portion of the heart; processing the measured electrophysiology information to identify one or more contact points that are potential treatment sites; and flagging the one or more identified potential treatment sites on the graphical representation. In addition, the method may include: receiving input that selects one or more of the identified potential treatment sites on the graphical representation of the three-dimensional model of the portion of the heart; and robotically moving the electrode to at least one selected treatment site.

In still another aspect of the invention, a method of generating a diagnosis map of at least a portion of a heart includes the steps of: a) inserting a catheter within a heart; b) using a robotic controller to move the catheter within the heart; c) detecting position information of the catheter and generating position information for a surface point on the surface of the heart; d) measuring electrophysiology information at the surface point and associating the measured electrophysiology information with the position information for the surface point at which the electrophysiology information was measured; e) repeating steps c) and d) for each of a plurality of surface points; and f) generating a three-dimensional surface model of the portion of the heart including position information for the plurality of surface points and the associated measured electrophysiology information. The three-dimensional surface model may optionally be stored on a storage medium. Additionally, the three-dimensional surface model may be presented as a graphical representation having information indicative of the measured electrophysiology information superimposed thereon.

An advantage of the present invention is a reduced exposure to radiation for both the patient and the physician, since the present invention reduces the time required to navigate the catheter to a target location and minimizes the need for fluoroscopy to locate the catheter within the patient.

Another advantage of the present invention is the ability to easily switch between automated robotic control and manual control of the catheter.

Still another advantage of the present invention is the ability to remotely interact with the robotic surgical system controlling the catheter.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 13b is the derivative of the plot in FIG. 13a.

DETAILED DESCRIPTION OF THE INVENTION

Robotic Surgical System

Figure 1:
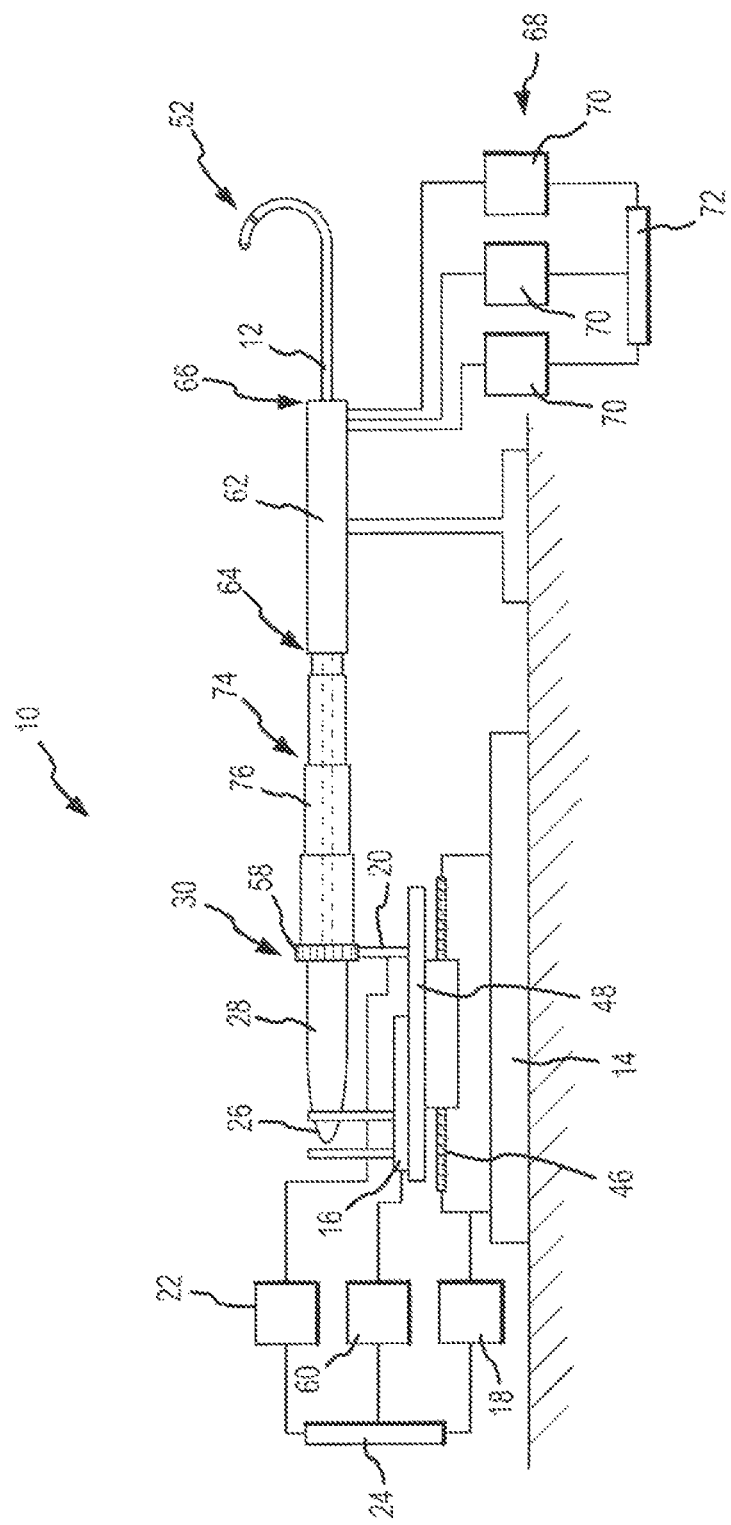
FIG. 1 is a schematic illustration of an embodiment of a robotic surgical system.

FIG. 1 schematically illustrates an embodiment of a robotic surgical system 10 for robotic manipulation and control of a medical device 12. Medical device 12 is preferably a catheter, which may be any type of catheter, including, by way of example only and without limitation, an ablation catheter, a guide wire catheter, an introducer catheter, a probe, or a stylet. It should be understood, however, that any other therapeutic, diagnostic, or assistive medical device may be controlled by robotic surgical system 10 without departing from the scope of the present invention. Such other devices include, but are not limited to, syringes, electrophoresis devices, iontophoresis devices, transdermal pharmaceutical delivery devices, myoblast delivery devices, stem cell delivery devices, ablation devices, stents, and pacemaker leads, which may be carried on or delivered by a catheter. It should further be understood that robotic surgical system 10 may be used to manipulate and control more than one medical device 12 in accordance with the quick installation and removal feature described herein. Accordingly, the terms "medical device," "probe," "therapeutic device," and "catheter" are used interchangeably herein.

Robotic surgical system 10 generally includes a track 14, a catheter holding device 16, a translation servo mechanism 18, a catheter deflection control mechanism 20, a deflection servo mechanism 22, and a controller 24 operatively coupled to at least one of translation servo mechanism 18 and deflection servo mechanism 22. Translation and deflection servo mechanisms 18, 22 may be any type of device for providing mechanical control at a distance, including continuous motors, stepper motors, hydraulic actuators, pulley systems, and other devices known to those of ordinary skill in the art. Catheter deflection control mechanism 20 and deflection servo mechanism 22 are collectively referred to herein as a "catheter deflection mechanism."

Catheter holding device 16 includes a catheter receiving portion 26. Catheter receiving portion 26 is configured to receive catheter 12 by installing a catheter control handle 28, located near a proximal end 30 of catheter 12, into catheter receiving portion 26. Preferably, catheter receiving portion 26 is adapted for quick installation and removal of any type of catheter 12 (or, as noted above, another medical device), thereby facilitating the installation of device 12 for control by robotic surgical system 10 and removal of device 12 for manual control (e.g., user manipulation of catheter control handle 28). Accordingly, catheter control handle 28 may be secured in catheter receiving portion 26 by a frictional fit or with one or more quick-release fasteners. Alternatively, the inner surface of catheter receiving portion 26 and the outer surface of catheter control handle 28 may include mating threaded portions to permit catheter control handle 28 to be screwed into catheter holding device 16. In other embodiments of robotic surgical system 10, catheter control handle 28 is clamped or strapped in place in catheter receiving portion 26. An adapter may also be used to facilitate the reception of catheter control handle 28 within catheter receiving portion 26.

Figure 2:
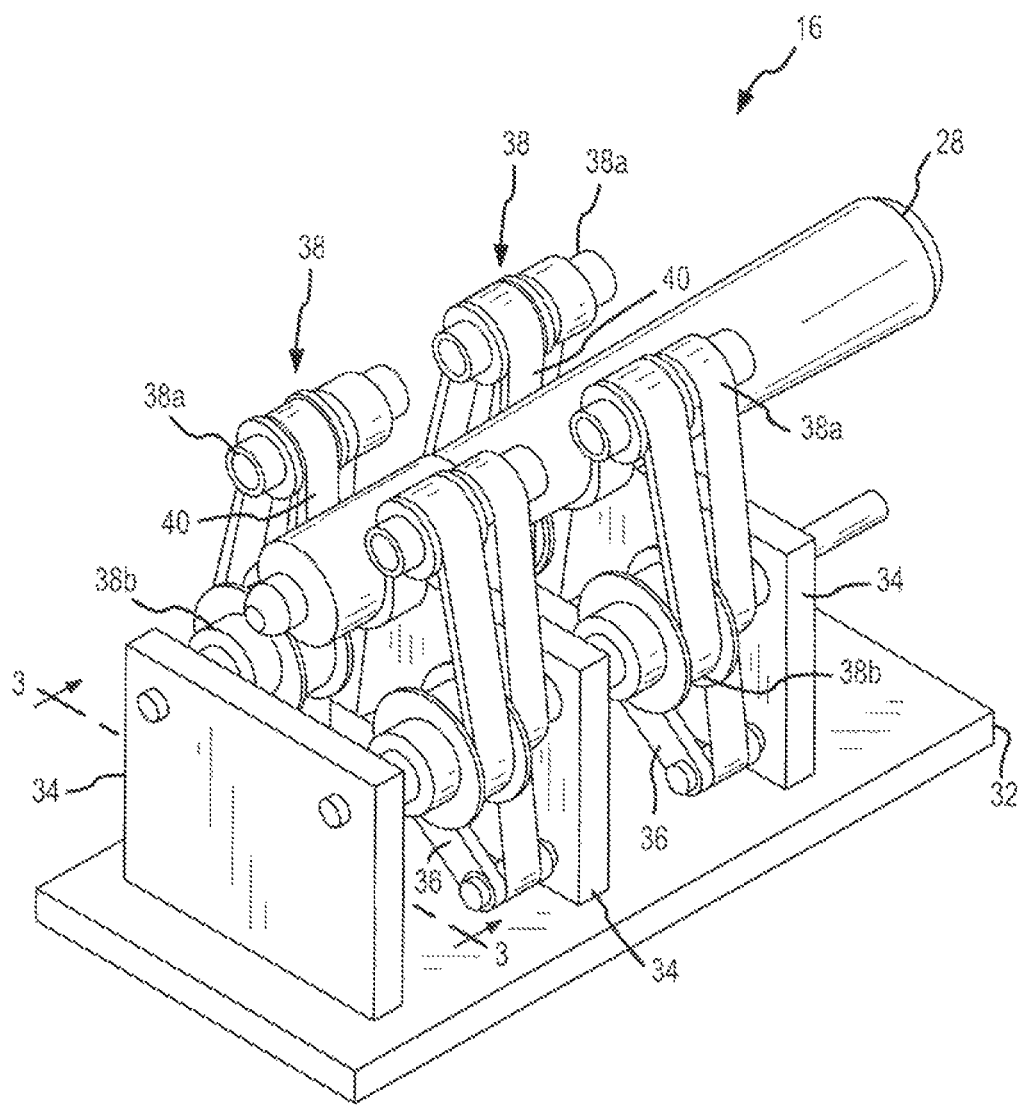
FIG. 2 is a perspective view of one embodiment of a catheter holding device with a catheter placed therein.
Figure 3:
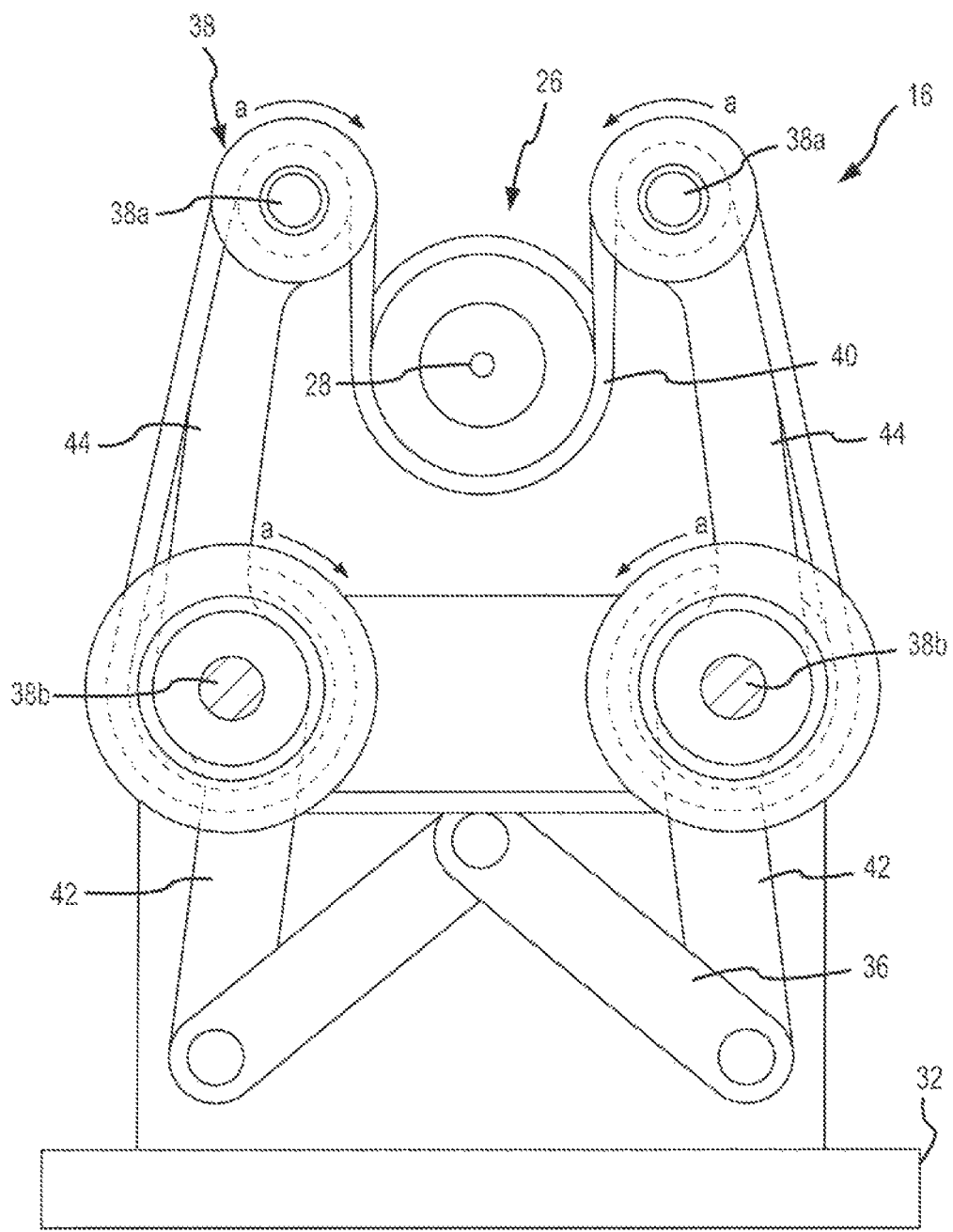
FIG. 3 is an end view of the catheter holding device of FIG. 2.

One embodiment of catheter holding device 16 is illustrated in FIGS. 2 and 3 with catheter control handle 28 placed, but not secured, therein. Catheter holding device 16 includes a base plate 32 and a plurality of upstanding support plates 34. Support plates 34 support cams 36, which are connected to pulley systems 38.

Figure 4:
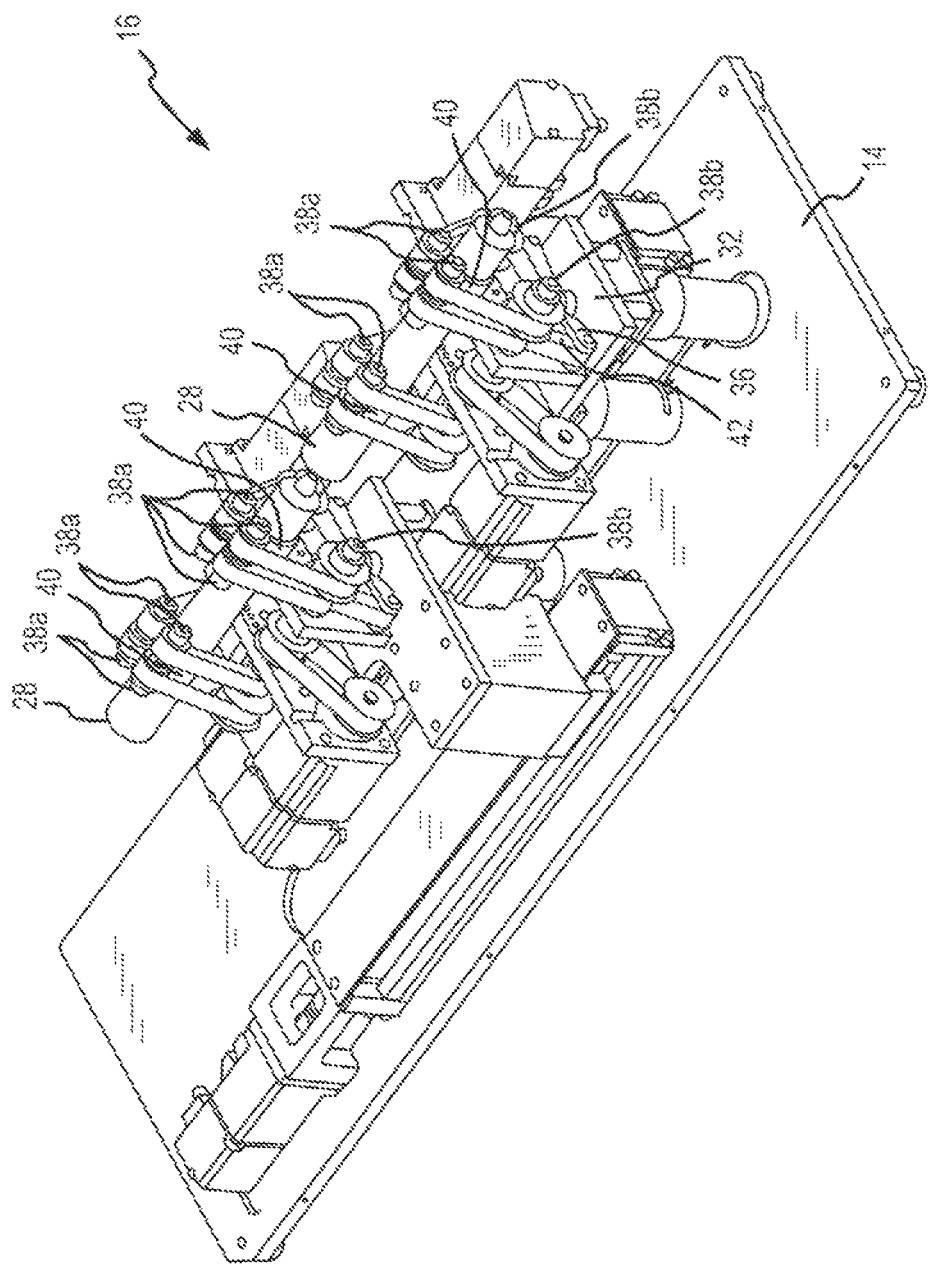
FIG. 4 is a perspective view of one embodiment of a catheter holding device with a catheter secured therein.
Figure 5:
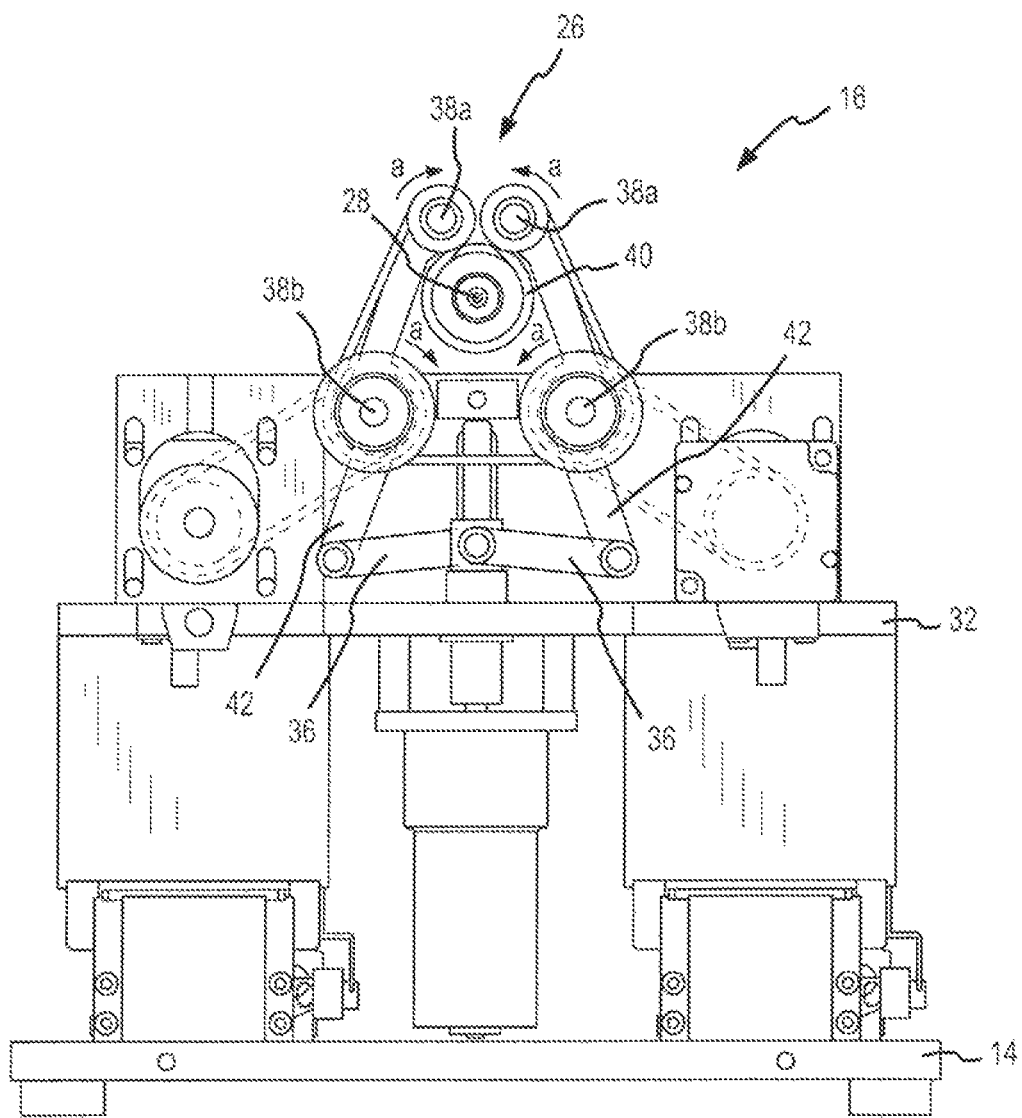
FIG. 5 is an end view of the catheter holding device of FIG. 4.

Catheter control handle 28 is received downwardly through an opening 40 into the catheter receiving portion 26 and onto belts 40 of pulley systems 38. As catheter control handle is urged downwardly, belts 40 rotate upper and lower pulleys 38a, 38b in the direction of arrows a. This, in turn, urges cams 36 downwards via links 42 and draws upper pulleys 38a, 38b towards one another via links 44, while simultaneously wrapping the belts 40 about catheter control handle 28. Catheter control handle 28 is thereby secured within catheter receiving portion 26 as shown in FIGS. 4 and 5. To remove catheter control handle 28 from catheter holding device 16, the user need only release cams 26, which reverses the process described above and opens catheter receiving portion 26.

Catheter holding device 16 is translatably associated with track 14. The phrase "translatably associated with" encompasses all types of relative lateral motion between catheter holding device 16 and track 14. For example, catheter holding device 16 may slide relative to track 14. Alternatively, catheter holding device 16 may move laterally along a screw mechanism 46, such as a worm gear, a lead screw, or a ball screw, attached to track 14. Preferably, catheter holding device 16 has a translation range relative to track 14 (i.e., the lateral distance that catheter holding device 16 can travel relative to track 14 between extremes) of at least about 5 cm, the approximate width of a human heart. More preferably, the translation range of catheter holding device 16 relative to track 14 is at least about 10 cm.

In the preferred embodiment of the invention, a carriage 48 is translatably mounted on track 14 via screw mechanism 46. Catheter holding device 16 is mounted on carriage 48 such that catheter holding device 16 translates relative to track 14 with carriage 48. For example, base plate 32 may be fixedly or removably mounted on carriage 48. Alternatively, catheter holding device 16 may be integrally formed with carriage 48 as a single assembly (i.e., base plate 32 and carriage 48 may be a single, unitary component). Likewise, in some embodiments of the invention, catheter holding device 16 may be translatably mounted directly on track 14 without an intervening carriage.

Translation servo mechanism 18 is operatively coupled to catheter holding device 16 and adapted to control translation of catheter holding device 16 relative to track 14 in order to adjust the lateral position of catheter holding device 16 along track 14. Preferably, translation servo mechanism 18 is operatively coupled to carriage 48 in order to move carriage 48, and therefore catheter holding device 16 mounted thereon, laterally along track 14. In the embodiment shown in FIG. 1, translation servo mechanism 18 drives screw mechanism 46, thereby moving carriage 48 laterally therealong.

Deflection servo mechanism 22 is operatively coupled to and adapted to control catheter deflection control mechanism 20. In the preferred embodiment of the invention, deflection servo mechanism 22 is operatively coupled to catheter deflection control mechanism 20 such that deflection servo mechanism 22 can rotate catheter deflection control mechanism 20. Either or both of deflection servo mechanism 22 and catheter deflection control mechanism 20 may be mounted on carriage 48 in order to simplify the transmission system linking deflection servo mechanism 22 and catheter deflection control mechanism 20. In some embodiments of robotic surgical system 10, catheter deflection control mechanism 20 is incorporated in catheter holding device 16, for example by utilizing pulley systems 38, and in particular belts 40, as further described below. One of ordinary skill in the art will appreciate, however, that catheter deflection control mechanism 20 may also be separated from catheter holding device 16 without departing from the spirit and scope of the present invention.

Controller 24 is adapted to control at least one of translation servo mechanism 18 and deflection servo mechanism 22 in order to navigate catheter 12 received in catheter holding device 16. It should also be noted that the use of multiple controllers to control translation servo mechanism 18 and deflection servo mechanism 22 is regarded as within the scope of the present invention. Throughout this disclosure, the term "controller" refers to a device that controls the movement or actuation of one or more robotic systems (that is, the component responsible for providing command inputs to the servo mechanisms). One of ordinary skill in the art will understand how to select an appropriate controller for any particular mechanism within robotic surgical system 10. Further, the term "controller" should be regarded as encompassing both a singular, integrated controller and a plurality of controllers for actuating one or more robotic systems.

Figure 6:
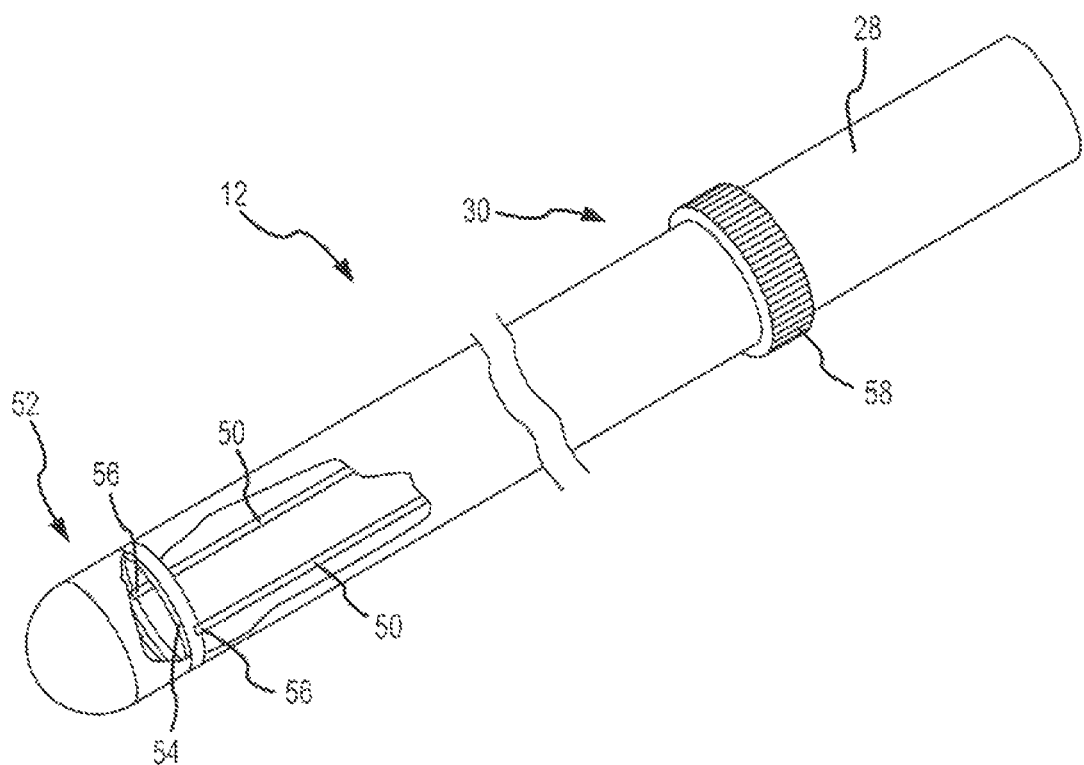
FIG. 6 illustrates an exemplary steerable catheter such as may be used in the robotic surgical system.

As shown in FIG. 6, catheter 12 is preferably a steerable catheter including at least one pull wire 50 extending from catheter control handle 28 near proximal end 30 of catheter 12 to a distal end 52 of catheter 12. Pull wires 50 may be coupled to at least one pull ring 54, also located near distal end 52 of catheter 12. When placed in tension, pull wires 50 deflect distal end 52 of catheter 12 into various configurations. As one of skill in the art will understand, additional pull wires 50 will enhance the deflection versatility of distal end 52 of catheter 12. For example, a single pull wire 50 with a single point of attachment to pull ring 54 will permit distal end 52 of catheter 12 to deflect on a single axis, and perhaps in only one direction, for example upwards relative to FIG. 6. By adding a second pull wire 50 (as shown in FIG. 6), or by looping a single pull wire 50 to have two points of attachment 56 to pull ring 54, distal end 52 of catheter 12 may be deflected in two directions, for example both upwards and downwards relative to FIG. 6. A catheter 12 with four pull wires 50 attached to pull ring 54 at about 90° intervals can deflect in four directions, for example upwards, downwards, and into and out of the plane of the paper relative to FIG. 6.

One or more catheter deflection actuators 58 may be provided on catheter control handle 28 to selectively tension one or more pull wires 50, thereby controlling the direction and degree of deflection of distal end 52 of catheter 12. In some embodiments, one or more knobs may be provided, rotation of which selectively tension one or more pull wires 50. It should be understood, however, that catheter deflection actuators 58 may take many other forms, including, but not limited to, sliders and switches, without departing from the spirit and scope of the present invention. Additionally, it is contemplated that rotating catheter control handle 28 itself may selectively tension pull wires 50 and deflect distal end 52 of catheter 12.

Returning to FIG. 1, when catheter control handle 28 is received within catheter receiving portion 26, catheter 12 translates relative to track 14 with catheter holding device 16, thereby providing a first degree of freedom permitting catheter 12 to be advanced into and retracted from a patient's body. Additionally, catheter 12 is operatively coupled to catheter deflection control mechanism 20 such that actuation of catheter deflection control mechanism 20 causes distal end 52 of catheter 12 to deflect, thereby providing a second degree of freedom to catheter 12. In particular, catheter deflection actuator 58 may be operatively coupled to catheter deflection control mechanism 20 such that catheter deflection control mechanism 20 can actuate catheter deflection actuator 58 to selectively tension one or more pull wires 50 and deflect the distal end 52 of catheter 12 by a desired amount in a desired direction.

In some embodiments of the invention, rotating catheter deflection control mechanism 20 will rotate catheter deflection actuator 58 in turn, thereby selectively tensioning one or more pull wires 50 within catheter 12. The transmission system between catheter deflection control mechanism 20 and catheter deflection actuator 58 may be a frictional fit provided, for example, by rubberized coatings surrounding catheter deflection control mechanism 20 and catheter deflection actuator 58. Alternatively, catheter deflection control mechanism 20 and catheter deflection actuator 58 may be coupled with mating gear teeth or knurling.

Referring specifically to the embodiment of catheter holding device 16 depicted in FIGS. 2-5, when catheter 12 is secured in catheter receiving portion 26, belts 40 frictionally engage catheter control handle 28. They may also engage catheter deflection actuator 58. Thus, if pulley system 38 is driven by deflection servo mechanism 22, belts 40 may rotate catheter control handle 28, catheter deflection actuator 58, or both, in order to selectively tension one or more pull wires 50 and deflect distal end 52 of catheter 12.

It should be understood that the particular configurations of catheter deflection control mechanism 20 and catheter deflection actuator 58 described above are merely exemplary and can be modified without departing from the spirit and scope of the invention. For example, if catheter deflection actuator 58 is a slider rather than a knob, catheter deflection control mechanism 20 may be suitably modified, or even replaced as a modular unit, to actuate a slider. This facilitates the quick connect/disconnect operation of robotic surgical system 10 by allowing easy installation and interconnection between off-the-shelf medical devices of varying construction and robotic surgical system 10.

As described above, the inclusion of additional pull wires 50 in catheter 12 increases the number of directions in which distal end 52 of catheter 12 can deflect. This is referred to herein as "deflection versatility." Where relatively few pull wires 50 (e.g., fewer than about four pull wires 50) are used, however, compensation for lost deflection versatility may be had by rotating catheter 12 about its axis. For example, in a catheter using only a single pull wire 50 with a single point of attachment to pull ring 54, permitting the catheter to deflect only in one direction, the catheter may be deflected in the opposite direction simply by rotating it 180° about its axis. Similarly, a catheter that can deflect in two directions 180° apart can be deflected in the directions midway therebetween by rotating the catheter 90° about its axis.

Accordingly, in some embodiments of the invention, catheter receiving portion 26 is rotatable. An example of such a rotatable catheter receiving portion is catheter receiving portion 26 defined by pulley system 38 depicted in FIGS. 2-5. A rotation servo mechanism 60 is operatively coupled to rotatable catheter receiving portion 26 and adapted to control rotatable catheter receiving portion 26. Thus, pulley system 38 may be driven by rotation servo mechanism 60, thereby engaging belts 40 to rotate catheter 12 about its axis.

If desired, rotation servo mechanism 60 may be mounted on carriage 48 or affixed to catheter holding device 16 such that rotation servo mechanism 60 translates relative to track 14 with catheter holding device 16. This arrangement creates a fixed-distance relationship between rotation servo mechanism 60 and catheter holding device 16, which can simplify the transmission system coupling rotation servo mechanism 60 to catheter holding device 16.

When installed in catheter holding device 16, catheter 12 rotates with catheter receiving portion 26, thereby providing a third degree of freedom to catheter 12 and compensating for low deflection versatility attributable to a relatively lower number of pull wires 50. Catheter receiving portion 26 is preferably rotatable at least about 360° about its axis, such that catheter 12 received therein is also rotatable at least about 360° about its axis, thereby facilitating deflection of distal end 52 of catheter 12 in substantially any direction, significantly enhancing the deflection versatility of the distal end 52 of the catheter 12. Catheter receiving portion 26 may also be designed to rotate about 720° or more about its axis.

Rotating catheter 12 by rotating catheter receiving portion 26 may cause inadvertent deflection of distal end 52 of catheter 12. As one skilled in the art will recognize from this disclosure, as catheter receiving portion 26 and catheter 12 rotate, catheter deflection actuator 58 may remain stationary, rather than rotating with catheter control handle 28, if the torque applied by rotation servo mechanism 60 is insufficient to overcome the inertia of catheter deflection control mechanism 20. That is, catheter deflection actuator 58 may bind against catheter deflection control mechanism 20, causing relative rotation between catheter control handle 28 and catheter deflection actuator 58. This relative rotation may result in uncommanded tensioning of one or more pull wires 50, inadvertently deflecting distal end 52 of catheter 12.

To maintain a substantially constant deflection as catheter 12 rotates, therefore, controller 24 may be operatively coupled to both rotation servo mechanism 60 and deflection servo mechanism 22. Controller 24 is adapted to control at least one of deflection servo mechanism 22 and rotation servo mechanism 60, and preferably to simultaneously control both deflection servo mechanism 22 and rotation servo mechanism 60, to maintain a substantially constant deflection of distal end 52 as catheter receiving portion 26 and catheter 12 rotate. For example, as controller 24 commands rotation servo mechanism 60 to rotate catheter receiving portion 26, controller 24 may simultaneously command deflection servo mechanism 22 to actuate catheter deflection control mechanism 20 to counter-rotate, thereby substantially eliminating relative rotation between the catheter deflection actuator 58 and catheter control handle 28, helping to maintain a substantially constant deflection of catheter 12. Alternatively, as controller 24 commands rotation servo mechanism 60 to rotate catheter receiving portion 26, it may simultaneously command deflection servo mechanism 22 to decouple catheter deflection control mechanism 20 from catheter deflection actuator 58, thereby permitting catheter deflection actuator 58 to rotate freely with catheter control handle 28. In either case, controller 24 may be configured to eliminate the need to couple deflection servo mechanism 22 and rotation servo mechanism 60 through a mechanical transmission system such as a differential. Further, though described herein as a single controller adapted to control the translation, deflection, and rotation servo mechanisms 18, 22, 60, multiple controllers may be used without departing from the spirit and scope of the present invention.

An introducer 62, preferably a steerable introducer, and most preferably an Agilis™ steerable introducer, may be provided as part of robotic surgical system 10. A proximal end 64 of introducer 62 is preferably stationary, while a distal end 66 of introducer 62 extends into a patient (not shown for clarity) to a location proximate a target site (the term "target" is used herein to refer to a location at which treatment or diagnosis occurs). Introducer 62 may be steerable via a robotic control system 68 including at least one servo mechanism 70 adapted to control distal end 66 of introducer 62 in at least one degree of freedom. Preferably, robotic control system 68 includes three servo mechanisms 70 adapted to control distal end 66 of the introducer 62 in three degrees of freedom (translation, deflection, and rotation), resulting in a total of six degrees of freedom for robotic surgical system 10, and at least one controller 72 adapted to control servo mechanisms 70. Similar control principles may be applied to steerable introducer 62 as are described herein with respect to robotic surgical system 10 and medical device 12.

One of ordinary skill in the art will appreciate that the deflection of distal end 52 of catheter 12 is a function not only of the input to catheter deflection actuator 58 (i.e., the selective tensioning of one or more pull wires 50), but also of the extent to which catheter 12 is advanced beyond a generally rigid sheath, such as introducer 62. That is, the further distal end 52 of catheter 12 is advanced beyond distal end 66 of introducer 62, the greater the deflection of distal end 52 of catheter 12 will be for a given input at catheter deflection actuator 58.

It is therefore desirable to calibrate the deflection of distal end 52 of catheter 12 in terms of both catheter deflection control mechanism inputs and extensions of catheter 12 beyond distal end 66 of introducer 62. By robotically actuating catheter deflection control mechanism 20 between extremes (e.g., commanding a complete rotation of catheter deflection actuator 58) and measuring the resulting deflection of distal end 52 of catheter 12 (e.g., using a localization system), catheter deflection control mechanism inputs may be correlated with deflections of distal end 52 for a given extension of catheter 12 beyond distal end 66 of introducer 62. A similar process may be performed for a multiple different extensions of catheter 12 beyond distal end 66 of introducer 62, resulting in a family of calibration curves relating catheter deflection control mechanism inputs to deflections of distal end 52 of catheter 12. Each curve corresponds to a particular extension of catheter 12 beyond distal end 66 of introducer 62; the amount of extension of catheter 12 beyond distal end 66 of introducer 62 may be derived, at least in part, from the amount of translation of catheter holding device 16 relative to track 14.

To create a substantially sterile field around catheter 12 outside the patient's body, an expandable and collapsible tubular shaft 74 substantially surrounds at least a portion of catheter 12, such as the region of catheter 12 between catheter holding device 16 and proximal end 64 of introducer 62. Preferably, shaft 74 is sterilized before use along with other relevant components of robotic surgical system 10. As catheter holding device 16 translates to advance catheter 12 into the patient (i.e., to the right in FIG. 1), tubular shaft 74 collapses upon itself. Contrarily, as catheter holding device 16 translates to retract catheter 12 from the patient (i.e., to the left in FIG. 1), tubular shaft 74 expands. Preferably, tubular shaft 74 is assembled from a plurality of telescoping tubular elements 76. It is contemplated, however, that tubular shaft 74 may alternatively be an accordion-pleated or other expandable and collapsible structure.

Figure 7:
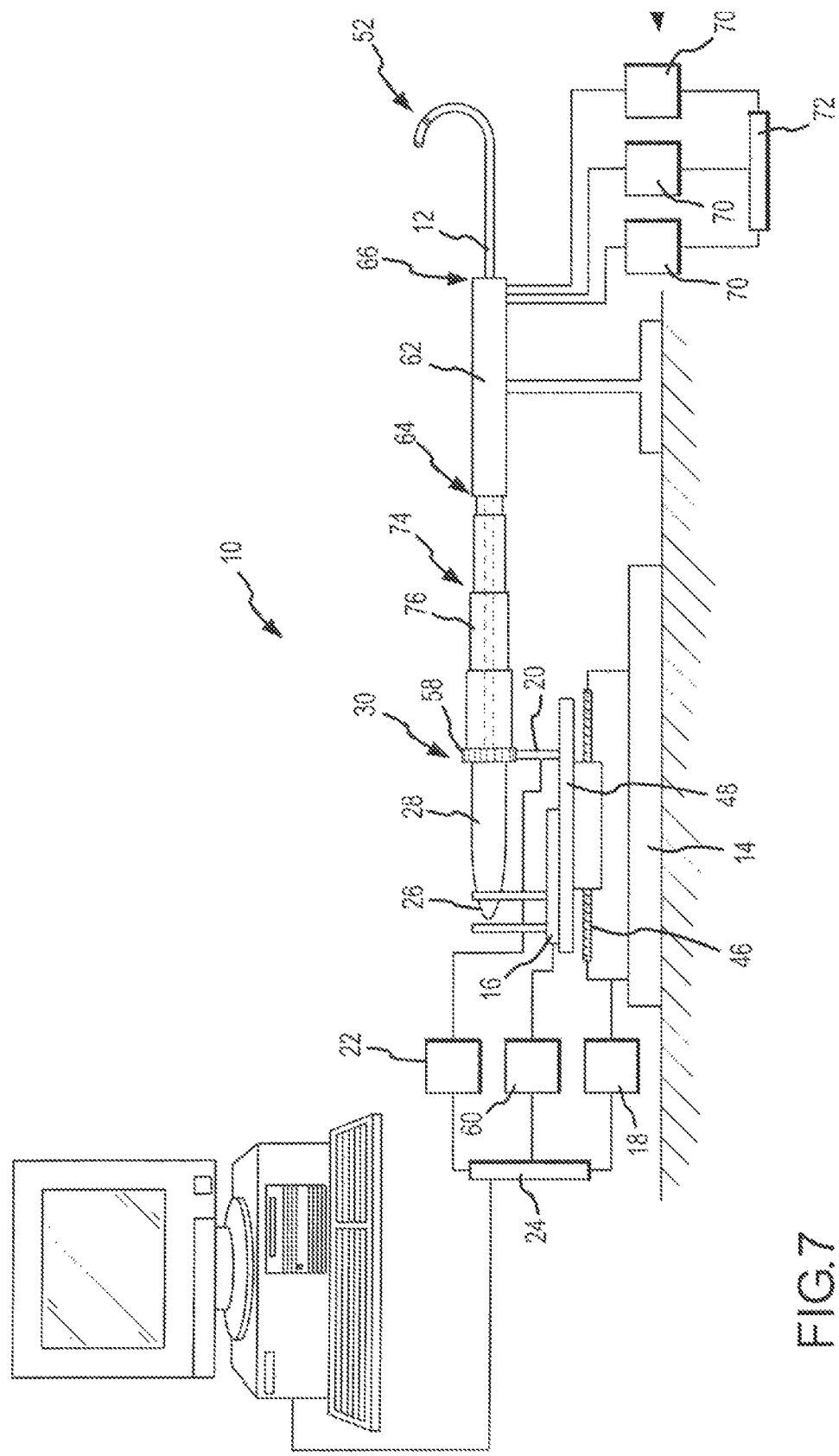
FIG. 7 depicts automatic control of the robotic surgical system according to a predetermined program.
Figure 8:
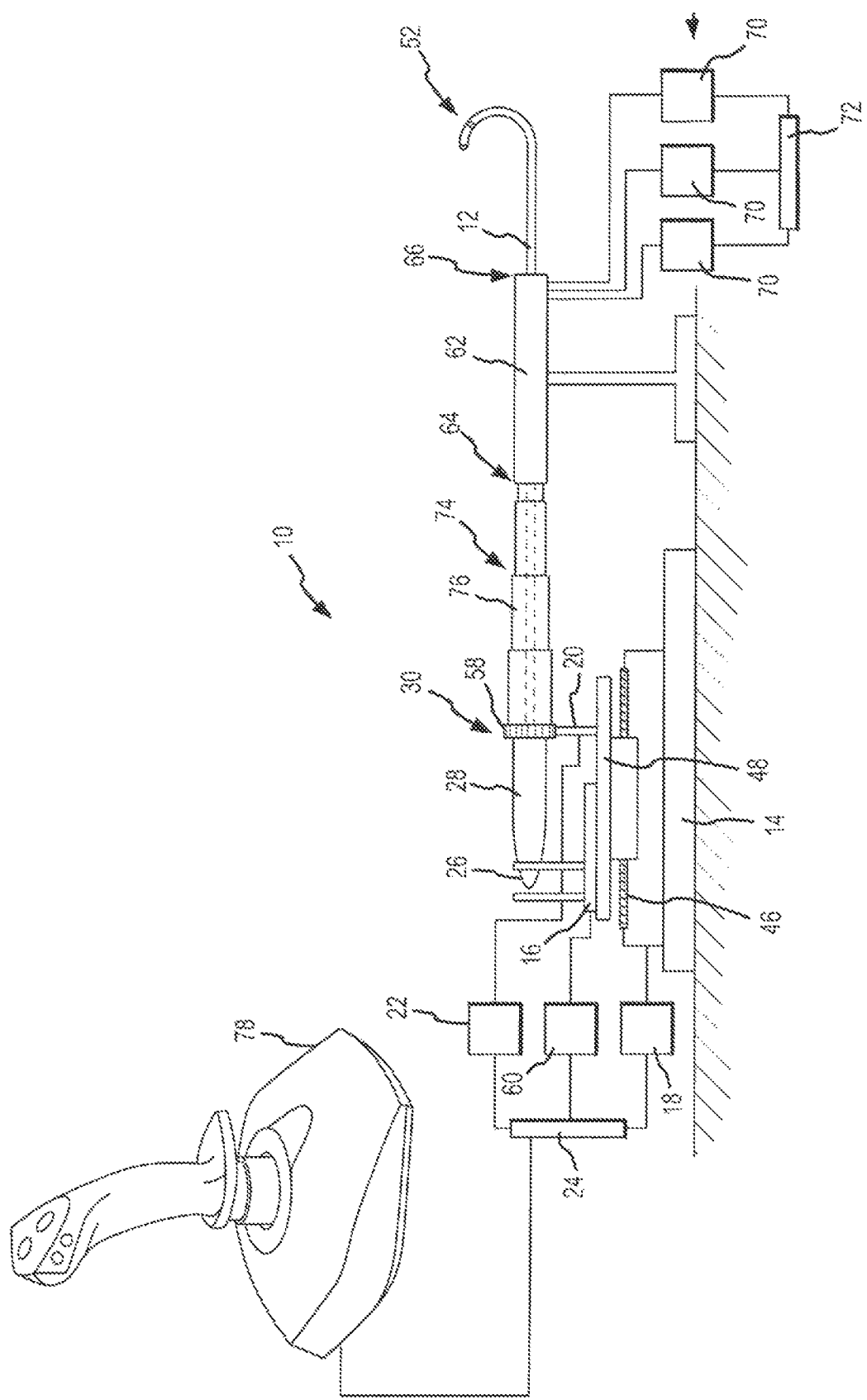
FIG. 8 depicts a user manually controlling the robotic surgical system via an input device.

As depicted in FIGS. 7 and 8, robotic surgical system 10 may be employed to robotically navigate catheter 12 into and through the patient and to one or more sites, which may be target sites, within the patient's body by actuating one or more of translation servo mechanism 18, deflection servo mechanism 22, and rotation servo mechanism 60 (if present) via controller 24. Robotic surgical system 10 may operate automatically according to a computerized program as executed by controller 24 (FIG. 7). It is also contemplated that the user, who may be a surgeon, cardiologist, or other physician, may control robotic surgical system 10 through an appropriate set of controls 78, such as a three-dimensional joystick (e.g., a joystick with three input axes), a steering yoke, or another suitable input device or collection of such devices permitting the user to robotically steer catheter 12 (FIG. 8).

Figure 9:
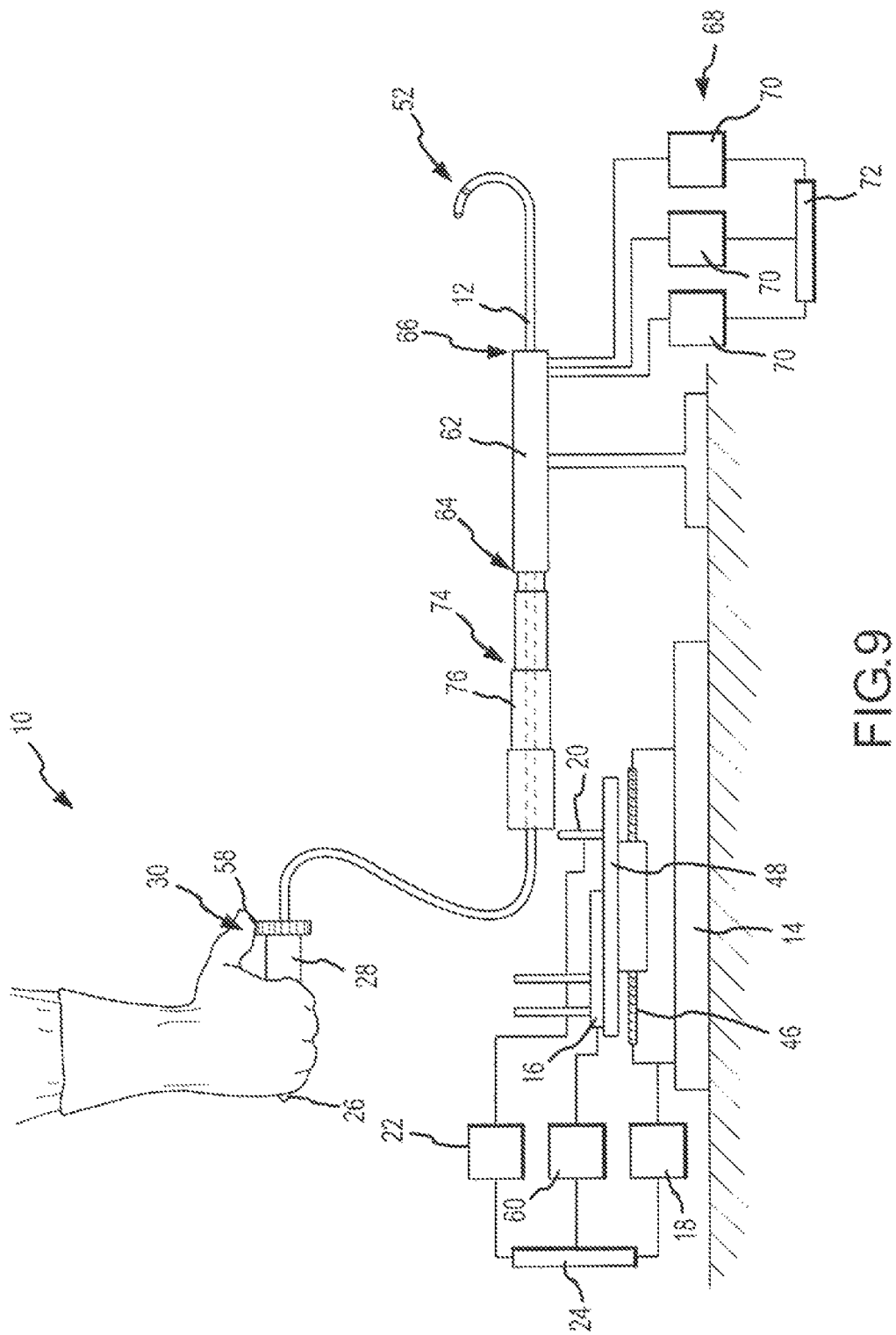
FIG. 9 depicts the user of FIG. 8 manually controlling the steerable catheter after having removed it from the robotic surgical system.

As described above, catheter 12 can be quickly and easily disconnected from catheter holding device 16. Thus, if the user desires to manually control catheter 12 at any point during the procedure, the user may disconnect catheter 12 from the catheter holding device 16 as described above. The user may navigate catheter 12 manually for as long as desired, and then replace it into catheter holding device 16 and resume robotic control. FIG. 9 illustrates the user manually operating catheter 12 after having removed it from catheter holding device 16.

In some embodiments of the invention, multiple robotic surgical systems controlling multiple medical devices may be employed during a procedure. For example, a first robotic surgical system may control an ultrasonic imaging transducer, while a second robotic surgical system may control an ablation catheter. A single controller, or multiple cooperating controllers, may coordinate the multiple medical devices and the multiple robotic surgical systems, for example in conjunction with a single localization system, or alternatively by utilizing data from the ultrasonic imaging transducer to control the movement of the ablation catheter.

Robotic surgical system 10 facilitates precise and accurate navigation of medical device 12 within the patient's body. In addition, since medical device 12 is manipulated primarily robotically, the physician will experience considerably less fatigue during the surgical procedure. Furthermore, robotic control permits a substantially increased degree of complexity in the control and actuation mechanisms that may be incorporated into medical device 12 over those that may be used in a medical device 12 intended solely for human control, enabling an increase in the versatility of medical device 12.

Contact Sensing

Figure 10:
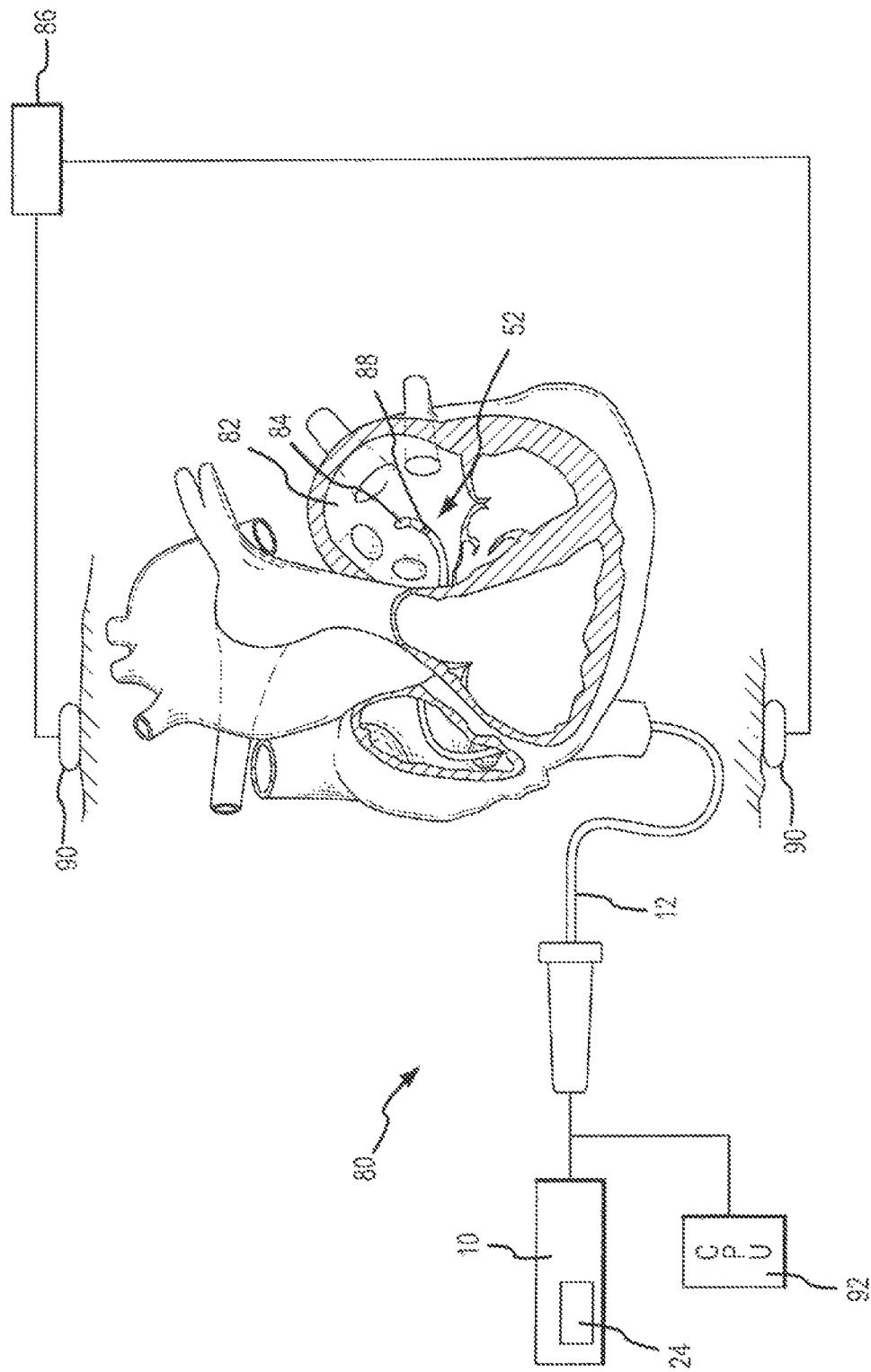
FIG. 10 schematically illustrates a contact sensing surgical system.

FIG. 10 schematically illustrates a surgical system 80 equipped to sense contact between a probe, such as catheter 12, and a tissue surface 82, such as a cardiac wall. Probe 12 includes a sensor or instrument 84 carried thereon, preferably at distal end 52 of probe 12, for measuring the value of a parameter (referred to herein as P) of tissue surface 82 either periodically (that is, with a relatively fixed interval between measurements) or episodically (that is, with a variable interval between measurements). Preferably, sensor 84 is an electrophysiology sensor capable of measuring one or more electrophysiology characteristics, including, but not limited to, impedance, phase angle, electrogram amplitude, optical feedback, and ultrasonic feedback.

To facilitate precise determination of the distance traveled by probe 12 between measurements of the tissue parameter (referred to herein as Δs), a precisely calibrated system is utilized. The precisely calibrated system may be a robotically controlled system to move probe 12 within the patient's body, such as robotic surgical system 10 described herein. It is also contemplated that measurements of the position of probe 12 within the patient's body may be made using a using a precisely locally- or universally-calibrated positional feedback (i.e., localization) system 86 in conjunction with a location or position electrode 88 carried on probe 12. Preferably, the positional feedback system is the Ensite NavX™ system of St. Jude Medical, Inc., which includes pairs of electrodes 90 defining measurement axes by which the position of probe 12 may be measured. One of ordinary skill in the art will appreciate that other localization systems, such as the CARTO navigation system from Biosense Webster, Inc., may also be employed. Only one pair of electrodes 90 is illustrated; one of skill in the art will appreciate that additional pairs of electrodes 90 may be used if additional measurement axes are desired.

A processor monitors the value of the tissue parameter measured by sensor 84 as probe 12 moves within the patient's body. The processor may be incorporated in a computer system 92. For purposes of this disclosure, a single processor within computer system 92 will be referred to, though it is contemplated that multiple computer systems 92 and/or multiple processors within a single computer system 92 may be used to practice the various aspects of the present invention. Further, one or more processor functions described herein may be integrated in a single processor without departing from the scope of the present invention.

As described above, probe 12 may be moved by a robotically-controlled system capable of precise movements on the order of less than about 5 mm, more preferably on the order of less than about 2 mm, and most preferably on the order of less than about 1 mm. Alternatively, the movements of probe 12 are precisely measured by a positional feedback system 86 with a margin of error of less than about 5 mm, preferably less than about 2 mm, and more preferably less than about 1 mm. For a given, precisely determined Δs (e.g., as precisely moved by robotic surgical system 10 or precisely measured by positional feedback system 86), a corresponding amount and rate of change in the tissue parameter between measurements can be anticipated for a situation where there is no change in the proximity or degree of contact between probe 12 and tissue surface 82.

The processor monitors the tissue parameter for an indicator of proximity or degree of contact between probe 12 and tissue surface 82 and indicates a change in the proximity or degree of contact between probe 12 and tissue surface 82 based on the monitored tissue parameter. In particular, the processor reports the change in either proximity or degree of contact based on either the amount of change in the tissue parameter or the rate of change in the tissue parameter between measurements, and preferably between successive measurements, thereof. The term "proximity" refers to the relationship between probe 12 and tissue surface 82 when probe 12 is not in contact with tissue surface 82; it is, in lay terms, a measure of how close probe 12 is to tissue surface 82. The term "degree of contact" refers to the relationship between probe 12 and tissue surface 82 when probe 12 is in contact with tissue surface 82; it is, in lay terms, a measure of how hard probe 12 is pressing into tissue surface 82.

Figure 11:
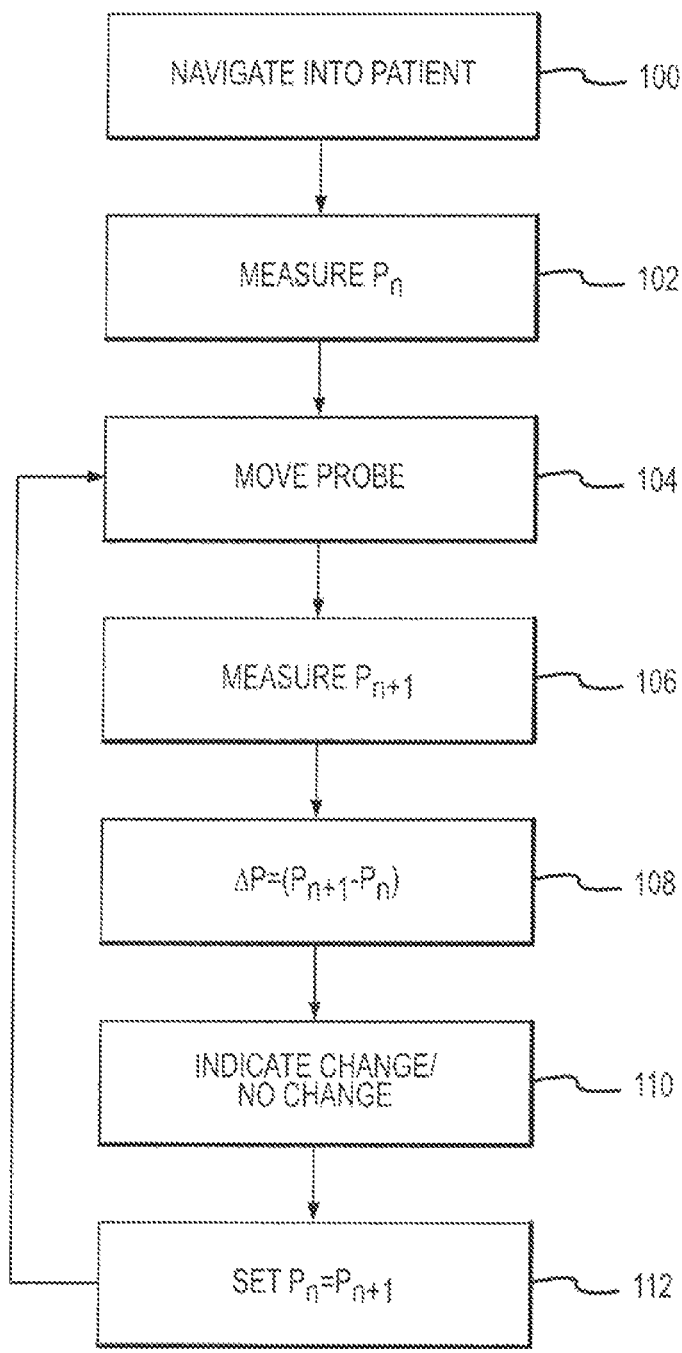
FIG. 11 is a high-level flowchart of a contact sensing methodology.

A contact sensing method is illustrated in the high-level flowchart of FIG. 11. Probe 12 is navigated into the patient's body and into meaningful proximity with tissue surface 82 in step 100. The term "meaningful proximity" refers to probe 12 being sufficiently close to tissue surface 82 such that sensor 84 can capture useful electrophysiology information about surface 82, and thus encompasses both contact and non-contact relationships between probe 12 and tissue surface 82.

Once inside the patient's body, probe 12 is moved using a calibrated system, such as robotic surgical system 10, moved and located using a calibrated system, such as positional feedback system 86, or both. As probe 12 moves, the tissue parameter at distal end 52 of probe 12 is measured, either periodically or episodically, using sensor 84 (steps 102, 104, and 106). An amount of change (ΔP) in the measured tissue parameter between successive measurements ($P_n$ and $P_{n+1}$) is calculated in step 108. The processor then indicates a change in proximity or degree of contact between probe 12 and tissue surface 82 based upon the amount of change in the measured tissue parameter in step 110. That is, the processor provides the user and/or controller 24 controlling robotic surgical system 10 with an indication of either "change" or "no change" in the proximity or degree of contact based upon the amount of change in the measured tissue parameter. If desired, the process may be repeated as probe 12 continues to move through the patient's body by setting $P_n=P_{n+1}$ (step 112) and moving probe 12 to a new location (step 104) where a new $P_{n+1}$ is measured (step 106).

Figure 12A:
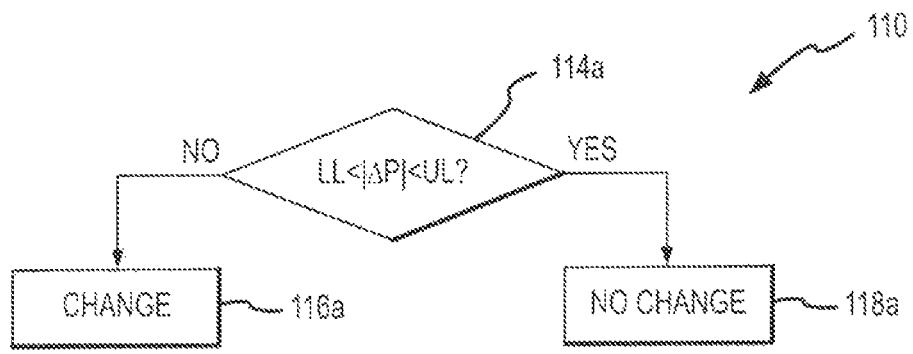
FIGS. 12a through 12o illustrate alternative implementations of the decision process for indicating a change in proximity or degree of contact in the high-level flowchart of FIG. 11.

A number of algorithms may be used to identify the change in proximity or degree of contact between probe 12 and tissue surface 82 in step 110. In a first algorithm, illustrated in FIG. 12*a*, the amount of change in the measured tissue parameter (ΔP) is compared to a predetermined range of values ranging from a lower limit (LL) to an upper limit (UL) in step 114*a*. (In FIGS. 12*a* through 12*o*, absolute values are used in order to account for potential negative values of ΔP.) A change is indicated when the amount of change in the measured parameter falls outside the predetermined range of values (step 116*a*); no change is indicated when the amount of change in the measured parameter falls within the predetermined range of values (step 118*a*).

The predetermined range of values (that is, either or both of UL and LL) may be user selectable, and may correspond generally to the anticipated amount of change in the measured tissue parameter between measurements when there is no change in the proximity or degree of contact between probe 12 and tissue surface 82 for a given Δs. "Predetermined" is used herein to refer to values that are set in advance of applying the contact sensing algorithm; for example, the values (i.e., UL and LL) may be based upon a percentage variation in the anticipated change in the measured tissue parameter, which percentage may also be user selectable.

Figure 12B:
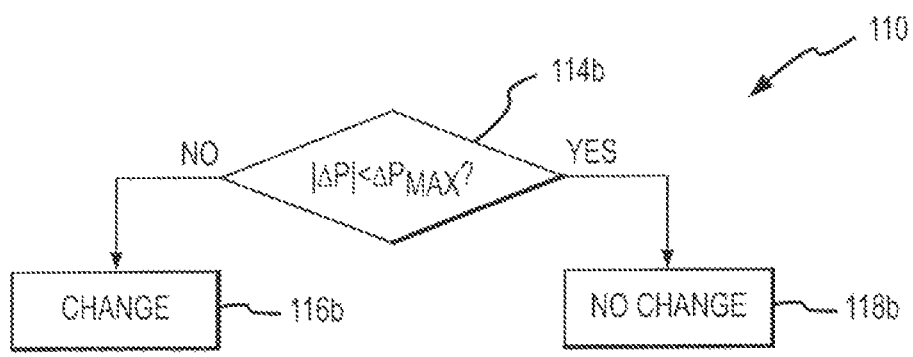
Figure 12C:
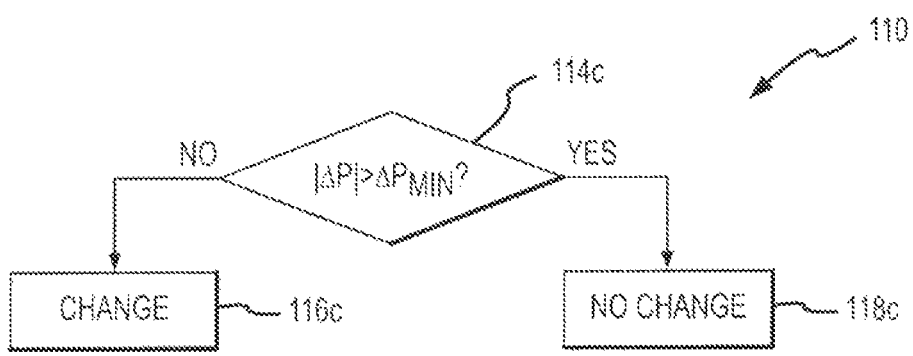
Figure 12D:
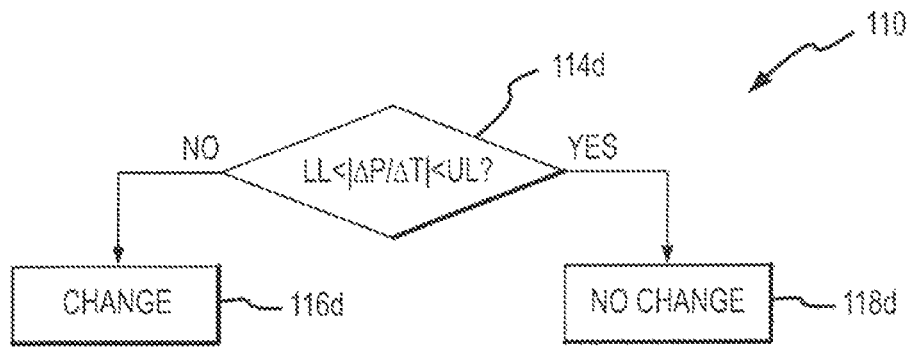
Figure 12E:
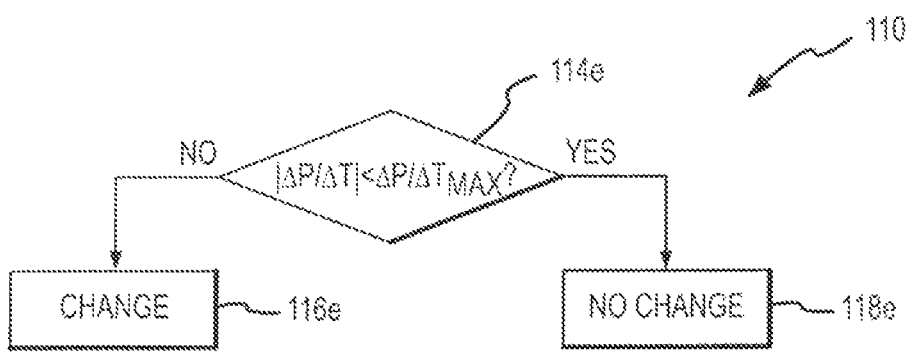
Figure 12F:
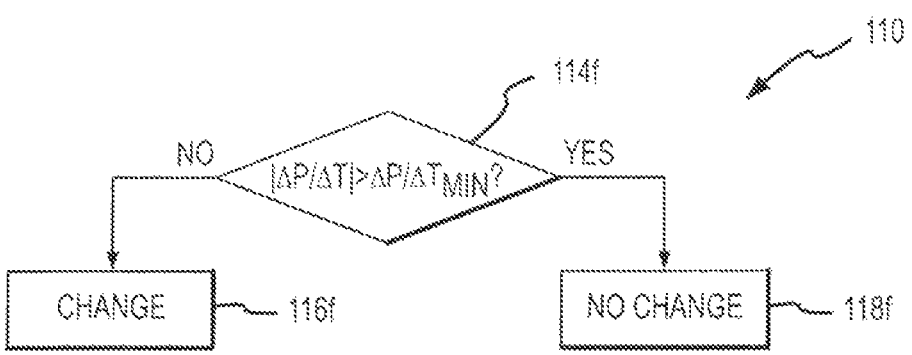
Figure 12G:
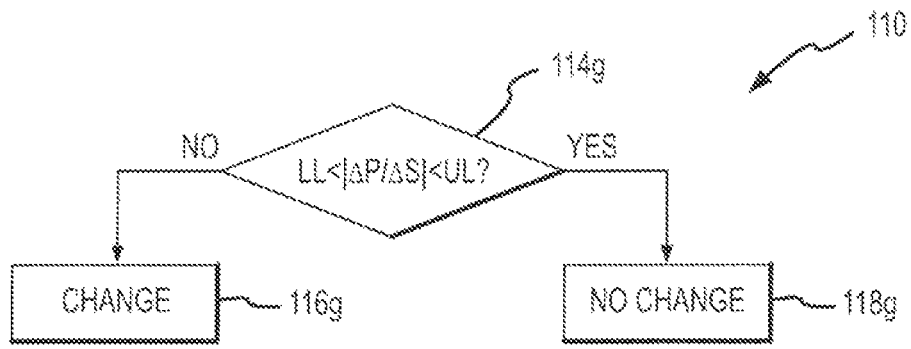
Figure 12H:
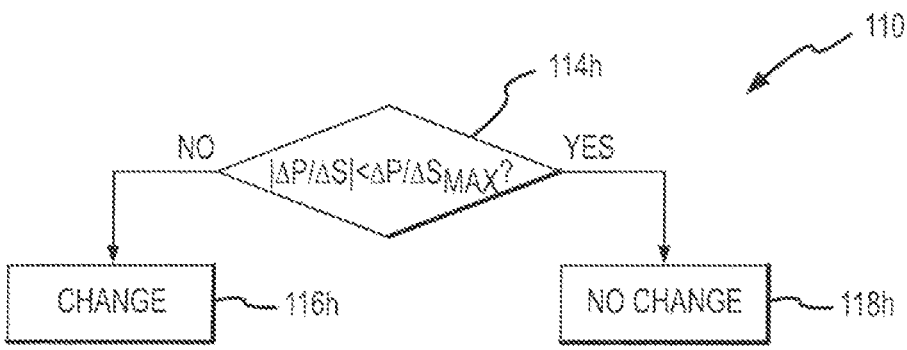
Figure 12I:
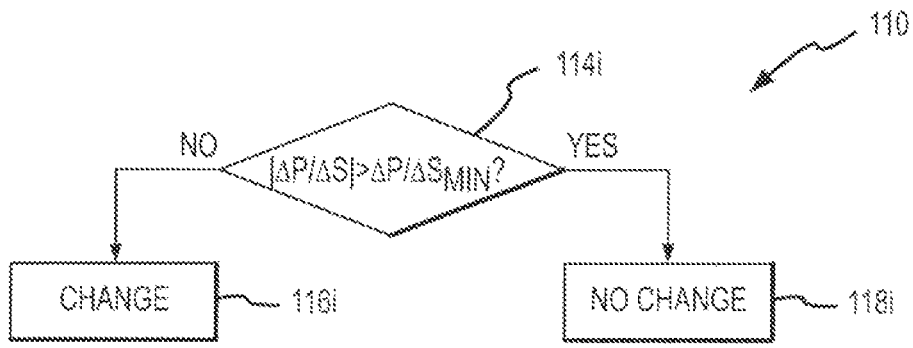
Figure 12J:
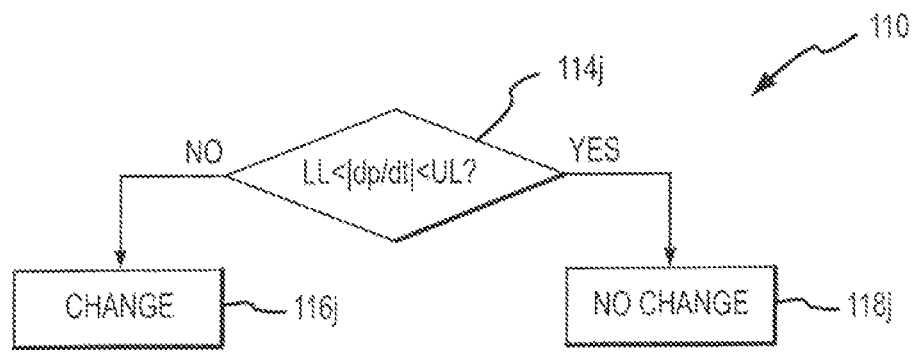
Figure 12K:
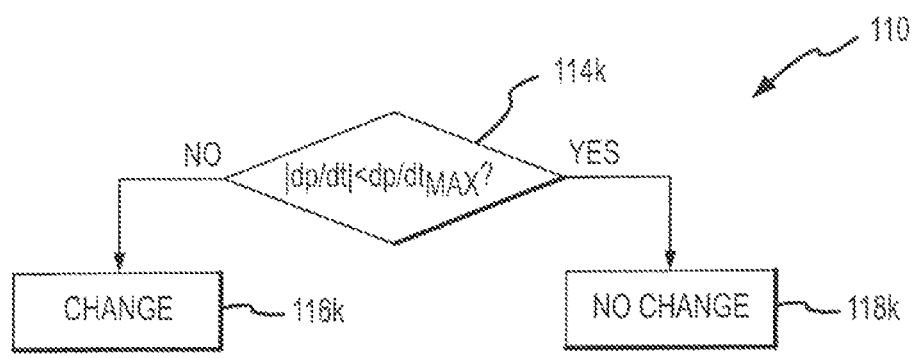
Figure 12L:
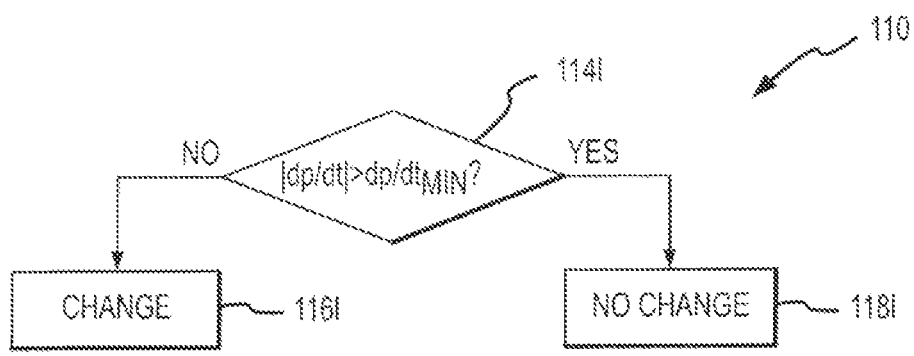
Figure 12M:
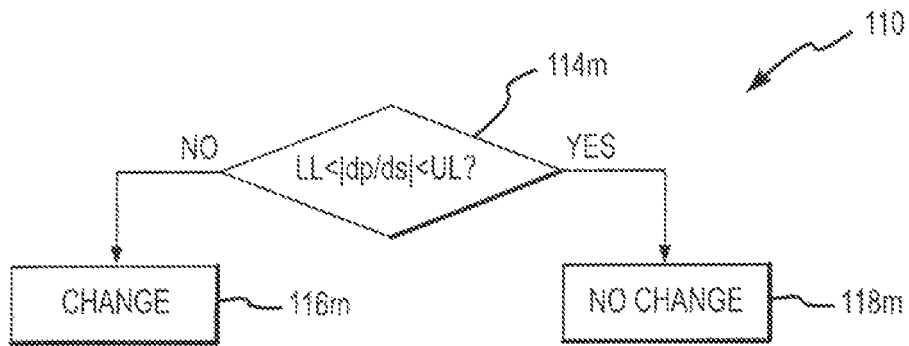
Figure 12N:
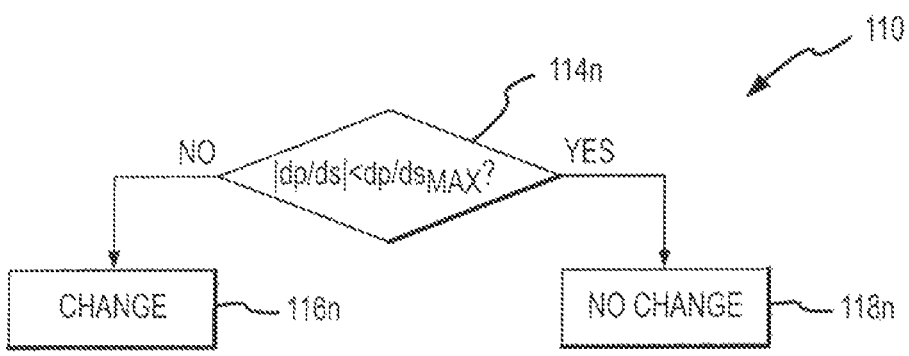
Figure 12O:
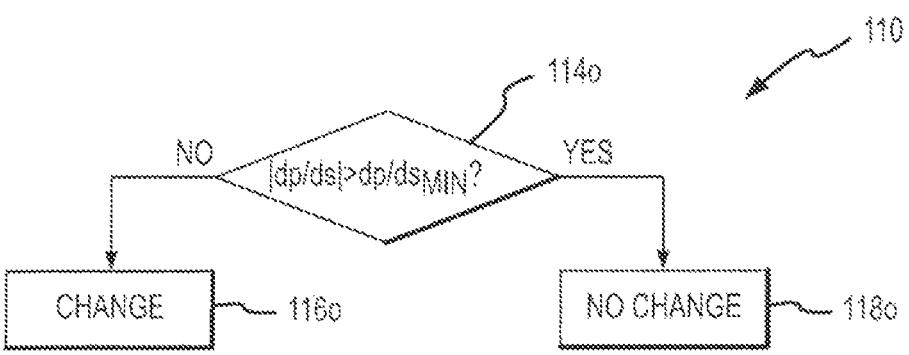

In other algorithms, the amount of change in the measured tissue parameter is compared to a change threshold, with the change indication based upon whether or not the measured tissue parameter crosses the change threshold. For example, as shown in FIG. 12*b*, the change threshold may correspond generally to the maximum anticipated amount of change in the measured tissue parameter between successive measurements for a given Δs ($ΔP_{MAX}$). Thus, no change in proximity or degree of contact would be indicated when the amount of change is less than the change threshold, and a change in proximity or degree of contact would be indicated when the amount of change is greater than the change threshold. It is also contemplated that the algorithm may be modified as shown in FIG. 12*c*, such that the threshold corresponds generally to the minimum anticipated amount of change in the measured tissue parameter between successive measurements for a given Δs ($ΔP_{MIN}$), which would reverse the conditions for indicating change or no change in proximity or degree of contact. The change threshold may be user selectable, and may be calculated as a percentage variation in the anticipated amount of change in the measured tissue parameter for a given Δs, which percentage may itself be user selectable.

In still other algorithms, the change in proximity or degree of contact is indicated based upon a rate of change in the measured tissue parameter with respect to either the time between measurements (ΔP/Δt) or the distance traveled by probe 12 between measurements (ΔP/Δs). The rate of change may also be calculated as a derivative of the measured tissue parameter with respect to time (dP/dt) or probe distance traveled (dP/ds). The rate of change may be calculated as a first derivative of the tissue parameter, a second derivative of the tissue parameter, or any further derivative of the tissue parameter. One of skill in the art will recognize that any of these variables may be calculated from the amount of change in the measured tissue parameter and the time between measurements or the precisely determined distance traveled by probe 12 between measurements. The decision processes for indicating change in proximity or degree of contact based upon rate of change variables are substantially analogous to the algorithms described with respect to the amount of change in the measured tissue parameter (i.e., comparison to a predetermined range of values or comparison to a rate of change threshold). These alternative algorithms are illustrated in FIGS. 12*d*-12*o*.

Figure 13A:
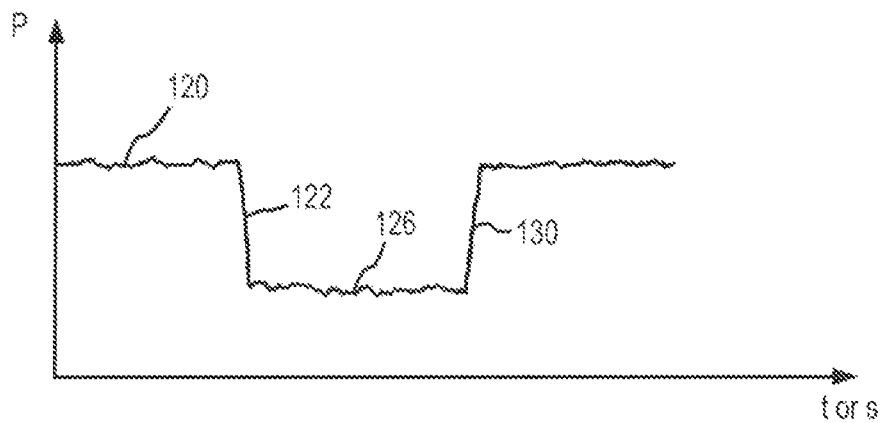
FIG. 13a is an exemplary plot of tissue parameter versus either time or probe distance as measured by a contact sensing surgical system.
Figure 13B:
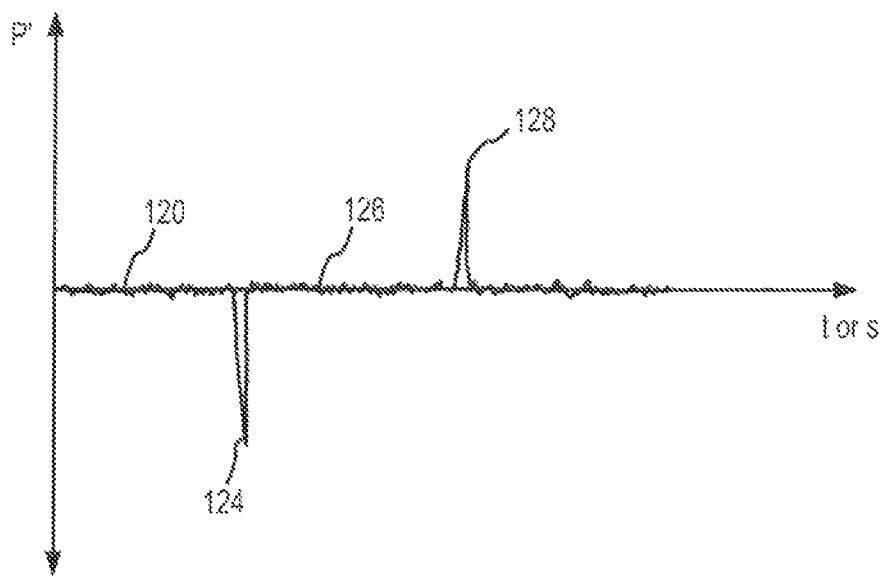

FIG. 13*a* is a representative chart of the measured tissue parameter as a function of time (t) or probe distance traveled (s), while FIG. 13*b* illustrates the derivative of the curve of FIG. 13*a*. Initially, in region 120, there is no change in proximity or degree of contact, so P varies only slightly. ΔP is thus quite small, so ΔP/Δt, ΔP/Δs, dP/dt, and dP/ds vary slightly about zero (dP/dt and dP/ds are illustrated in FIG. 13*b*).

When a change in proximity or degree of contact occurs, such as at point 122, P experiences a substantial change in a very short interval of time or probe distance traveled. Δ/Δt and ΔP/Δs are thus quite large, and the curve of FIG. 13*b* illustrating the derivative of the measured tissue parameter exhibits a corresponding spike 124 before returning to varying slightly about zero in region 126. A second spike 128 corresponds to a point 130 where another change in proximity or degree of contact occurs.

The contact sensing methods described above are useful in monitoring for a change indicative of probe 12 making contact with tissue surface 82, a change indicative of probe 12 breaking contact with tissue surface 82, or a change indicative of a change in the degree of contact between probe 12 and tissue surface 82. In the lattermost case, the method may provide an indicator of whether probe 12 is beginning to break contact with tissue surface 82 or is potentially being traumatically driven into tissue surface 82. This information may be used by the user and/or robotic surgical system 10 (e.g., controller 24) as feedback to adjust the movement of probe 12 to maintain a particular degree of contact with tissue surface 82 on an ongoing basis in order to improve the quality or efficiency of the medical treatment. For example, in an ablation procedure for the treatment of atrial fibrillation, one of ordinary skill will readily appreciate that a spike in a derivative of the tissue parameter, as shown in FIG. 13*b*, may indicate that the ablation catheter has broken contact with the cardiac surface and is therefore no longer creating a substantially continuous lesion and that appropriate corrective action is necessary to bring the ablation catheter back into contact with the cardiac surface. As another example, in a surface modeling procedure, the spike may indicate that the modeling probe has broken contact with the surface being modeled such that the collection of geometry points should be suspended in order to avoid capturing erroneous data.

Surface Modeling

Figure 14:
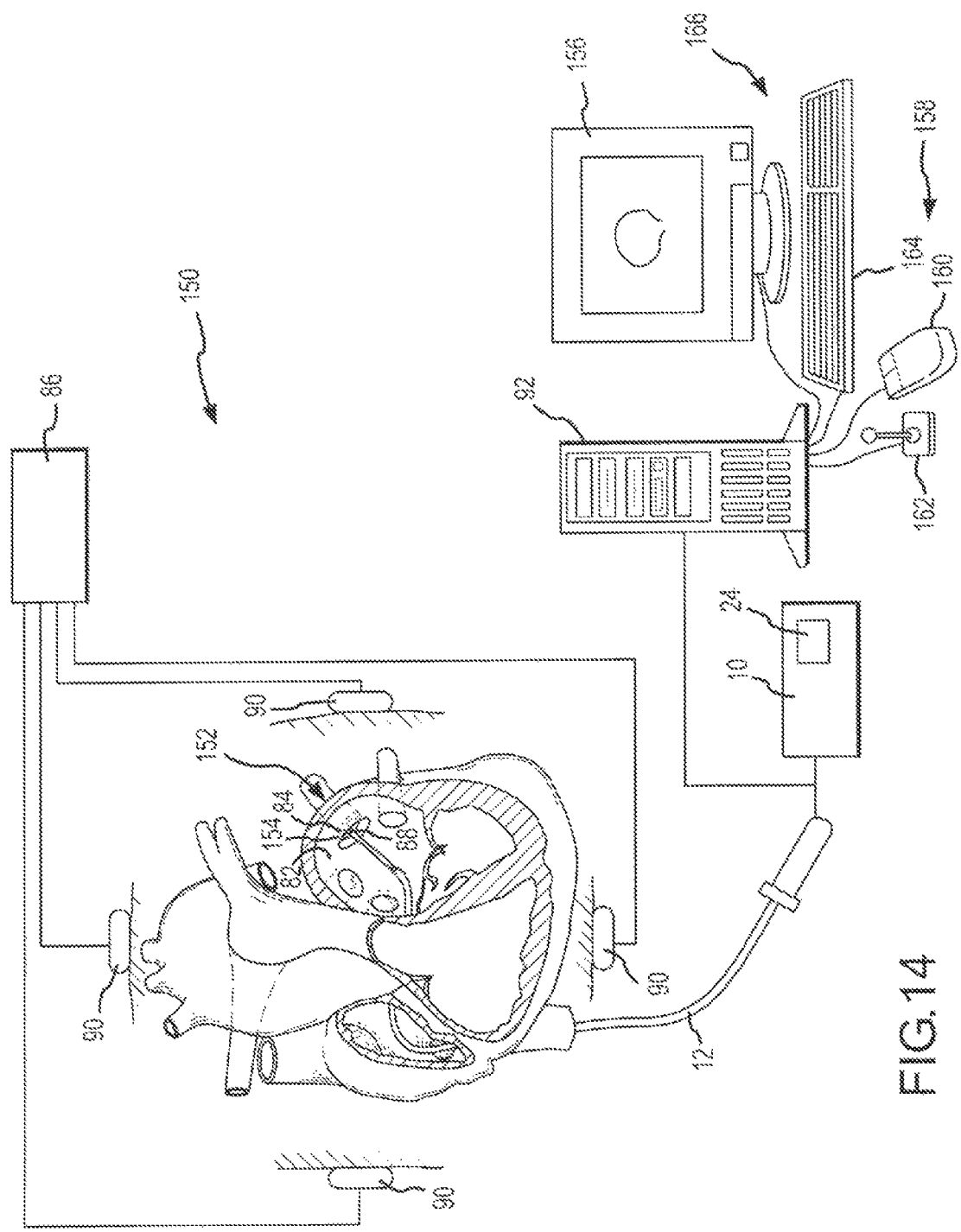
FIG. 14 illustrates a system for generating a three-dimensional model of a portion of a patient's body, optionally including diagnostic information.

FIG. 14 illustrates a system 150 for generating a three-dimensional model of at least a portion of the patient's body. Though system 150 will be described in the context of generating a three-dimensional model of the patient's heart chamber 152, it should be understood that system 150 and the method disclosed herein may also be employed to map the volume and tissue surface of any internal organ or other portion of the patient's body in which the user is interested.

Modeling system 150 includes electrode 154 for insertion into a portion of the patient's heart and a controller (once again denoted as controller 24, though an additional controller or controllers could be used) for robotically moving electrode 154 within the portion of the heart either randomly, pseudo-randomly, or according to one or more predetermined patterns. The term "predetermined pattern" is used to mean any pattern that is not random or pseudo-random, whether that pattern is computer- or user-dictated. Further, with reference to the phrase "within a portion of a heart," it should be appreciated that this does not refer to the movement of electrode 154 within the tissue itself (which could be traumatic), but rather to the movement of electrode 154 within a space that is interior to the patient's body (such as movement within the open space that defines heart chamber 152).

Electrode 154 may be a position, location, or mapping electrode, with the terms being used interchangeably herein. Controller 24 may be incorporated in robotic surgical system 10 described herein, in which case electrode 154 may be carried on catheter 12, preferably at or near distal end 52 of catheter 12 such that electrode 154 may be brought into contact with tissue surface 82 of heart chamber 152. It is also contemplated that electrode 154 may be located more proximally along catheter 12, for example adjacent to electrode 88. In the latter configuration, the relationship between electrode 154 and distal end 52 may be used to derive position information for distal end 52 from position information for electrode 154. It should be understood that carrying electrode 154 on a non-catheter probe, utilizing an alternative robotic control system to move electrode 154, and manually moving electrode 154 are all regarded as within the scope of the invention. It should further be understood that the use of both individual and multiple electrodes to practice the various aspects of the present invention is contemplated (i.e., electrode 88 and electrode 154 may be the same electrode).

Positional feedback system 86 detects position information of electrode 154 within heart chamber 152. Position detector 86 preferably includes a plurality of paired electrodes 90 defining measurement axes for locating electrode 154 within the patient's body by utilizing the electrical potentials measured by electrode 154. An example of a suitable positional feedback system 86 is disclosed in U.S. application Ser. No. 11/227,006, filed 15 Sep. 2005 (the '006 application) and U.S. provisional application No. 60/800,848, filed 17 May 2006 (the '848 application), both of which are hereby expressly incorporated by reference as though fully set forth herein. The terms "position detector," "positional feedback system," "mapping system," and "navigation system" are used interchangeably herein.

By detecting the position of electrode 154 multiple times as electrode 154 is moved within heart chamber 152, position detector 86 generates a plurality, or cloud, of location points defining the space occupied by heart chamber 152. Positional feedback system 86 need not determine whether a particular location point is a surface point or an interior point during the position detection step; the interior points will be resolved during subsequent processing. That is, the cloud of location points is generated indiscriminately, advantageously reducing the overhead and time required to collect the data set from which the three-dimensional model is generated. Thus, the cloud of location points preferably includes at least some location points on the surface of heart chamber 152 ("surface points") and at least some location points not on the surface of heart chamber 152 ("interior points"). The cloud of location points may be stored in a storage medium, such as a hard drive or random access memory (RAM), which may be part of computer system 92.

A modeling processor, which may be part of computer system 92, generates a three-dimensional model of heart chamber 152 from the cloud of location points. The three-dimensional model includes position information for a plurality of surface points describing a three-dimensional surface model of heart chamber 152. That is, after the cloud of location points is generated, the modeling processor identifies, isolates, and either disregards or eliminates the interior points by applying a surface construction or surface modeling algorithm to the plurality of location points. Preferably, the surface modeling algorithm employed is a shrink-wrap algorithm, though numerous other surface modeling algorithms are contemplated, including, but not limited to, convex hull algorithms (e.g., Qhull), alpha shapes, Hoppe's software, CoCone, and Paraform. The three-dimensional surface model may optionally be output as a graphical representation of heart chamber 152 on a display 154, which may also be part of computer system 92, or another output device. Further, the three-dimensional surface model may optionally be stored in a storage medium.

In use, electrode 154 is inserted within heart chamber 152, for example by advancing electrode 154 into heart chamber 152 on catheter 12 controlled by robotic surgical system 10. Next, electrode 154 is robotically moved within heart chamber 152. As described above, movement of electrode 154 within heart chamber 152 may be random, pseudo-random, or according to a predetermined pattern. Optionally, the predetermined pattern may include two distinct components: a first predetermined pattern until a determination is made that electrode 154 is in contact with tissue surface 82 of heart chamber 152, and a second predetermined pattern after electrode 154 has made contact with surface 82 of heart chamber 152. The contact sensing methodology described herein may be employed to determine when electrode 154 has made contact with surface 82 of heart chamber 152; to this end, it is contemplated that electrode 154 may function as sensor 84. The second predetermined pattern need not be substantially continuous along surface 82 of heart chamber 152; that is, electrode 154 may occasionally break contact with surface 82 of heart chamber 152 while following the second predetermined pattern such that electrode 154 "bounces" rather than "skates" along surface 82 of heart chamber 152.

For example, in some embodiments of the invention, electrode 154 may first measure a few initial location points in a region of heart chamber 152. Electrode 154 may then incrementally approach surface 82 of heart chamber 152; the contact sensing methodology described herein, or another suitable contact sensing methodology, may be utilized to determine when electrode 154 has contacted surface 82. A location point may be collected from surface 82 of heart chamber 152. A section of a model of surface 82 of heart chamber 152 may then be constructed from the initial location points and the surface location point, and electrode 154 may then be moved small distances, such as about 5 mm anti-normal to surface 82 and about 5 mm laterally to an unsampled region. This process may then be repeated as necessary to complete the cloud of location points.

As electrode 154 is moved within heart chamber 152, position information of electrode 154 is detected in order to generate the plurality of location points defining the space occupied by heart chamber 152. If electrode 154 is located at or near distal end 52 of catheter 12, position information may be stored directly; if electrode 154 is located more proximally, position information may be derived from the relationship between electrode 154 and distal end 52 prior to being stored. Detection of position information may be periodic (that is, with a relatively constant interval between successive measurements) or episodic (that is, with a variable interval between successive measurements). Detection may also be event-driven (for example, upon sensing a particular electrophysiological characteristic with sensor 84).

The three-dimensional model of heart chamber 152 is then generated from the plurality of location points by utilizing a surface construction algorithm, such as a shrink-wrap algorithm, to wrap or otherwise construct a surface around the plurality of location points. The three-dimensional model includes position information for at least some of the plurality of location points within heart chamber 152, preferably those location points describing a three-dimensional surface model of heart chamber 152. The model may be generated by processing the plurality of location points using a surface construction algorithm to identify and output the subset of the plurality of location points defining the three-dimensional surface model, and thus surface 82 of heart chamber 152. Interior points may be eliminated or simply disregarded by the surface construction algorithm. The subset of location points may define vertices for a plurality of triangles representing the three-dimensional surface model of heart chamber 152, and the triangles themselves may be generated by interconnecting the vertices. Once generated, the three-dimensional model may be presented as a graphical representation on display 156, permitting the user to interact intuitively with the model through input devices 158, which may include, but are not limited to, a mouse, trackball or other pointing device 160; a two- or three-dimensional joystick or control yoke 162; and a keyboard or keypad 164. Input devices 158 may be coupled to computer system 92. Optionally, one or more of input devices 158 may also serve as controls 78 permitting the user to robotically steer catheter 12.

As one of ordinary skill in the art will understand from the foregoing description, the present invention facilitates improved collection of location points. For example, manually controlled catheters may tend to follow repetitive or stereotypical patterns during sampling, and thus may not collection location points throughout the volume of the heart chamber. The robotically-controlled catheter of the present invention, however, is less susceptible to this shortcoming, in that it is capable of achieving the necessary control vectors to reach substantially all of the volume of the heart chamber. Further, the robotically-controlled catheter may be programmed to avoid repeat sampling of regions or to exclude repeatedly sampled location points, in the event that it is necessary to travel through a particular region more than once. As a result, the not only may the plurality of location points be improved, but also the time required to create the three-dimensional model may be reduced.

Diagnostic Data Mapping

Modeling system 150 may also be utilized to generate a diagnosis map for surface 82 of heart chamber 152 through the addition of an instrument for measuring physiological information, and preferably an instrument for measuring electrophysiology information, such as sensor 84. It should be understood that, though described herein as separate components, one or more of sensor 84, electrode 88, and electrode 154 may optionally be combined into a single component carried on probe 12. Sensor 84 measures electrophysiology information at a point on surface 82 of heart chamber 152 that is in meaningful proximity to probe 12. The diagnosis map contains information about the physiological characteristics of surface 82, for example the tissue impedance at various locations on surface 82.

As described above, controller 24 moves probe 12 to a plurality of locations within heart chamber 152, including into meaningful proximity with a plurality of surface points. A contact sensor, such as a force transducer, or the contact sensing methodology disclosed herein, may be employed to identify proximity or degree of contact between probe 12 and surface 82 of heart chamber 152, though, as one of ordinary skill in the art will appreciate, contact sensing is not necessary if the geometry of heart chamber 152 is already known, since proximity and contact information between probe 12 and surface 82 can be derived from the known geometry and positional feedback system 86.

Preferably, a processor, which may be part of computer system 92, causes probe 12 to automatically move into meaningful proximity with a plurality of surface points, for example by providing instructions to controller 24 incorporated in robotic surgical system 10 to actuate one or more of servo mechanisms 18, 22, 60 to translate, deflect, and/or rotate probe 12. It is also contemplated that the user may robotically steer probe 12 to the plurality of points via a suitable input device 158, such as joystick 162.

Sensor 84 detects electrophysiological information for at least some of the surface points, and preferably for each surface point. The processor associates the measured electrophysiological information with the position information for the surface point at which it was measured. As one of skill in the art should appreciate from this disclosure, the position information may be already known (e.g., through application of the surface modeling methodology disclosed herein) or may be gathered concurrently with the detection of electrophysiological information. Once position and electrophysiological information for the plurality of surface points has been gathered and associated as a plurality of surface diagnostic data points, the processor generates the diagnosis map of heart chamber 152 therefrom.

The diagnosis map may optionally be combined with the three-dimensional surface model of heart chamber 152 generated by the modeling processor or with another model of heart chamber 152 (e.g., an MRI- or CT-generated model). For example, the diagnosis map may be superimposed upon the three-dimensional surface model. If desired, the resultant three-dimensional diagnosis model, including both position information and physiological information, can be output on display 156 as a graphical representation. In addition, the diagnosis map or three-dimensional diagnosis model may be stored in a storage medium, which, as noted above, may be part of computer system 92.

Figure 15:
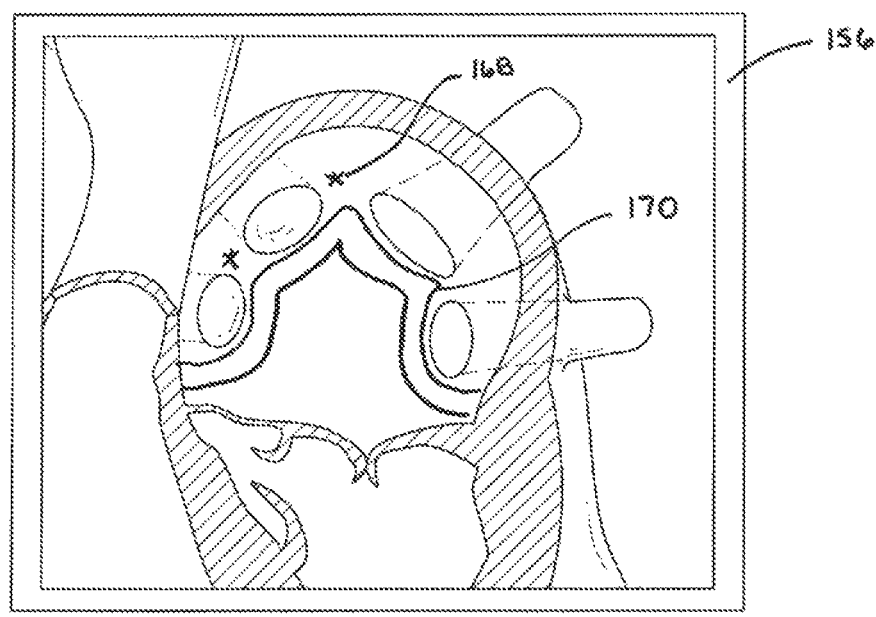
FIG. 15 illustrates a graphical representation of a three-dimensional model of a heart chamber including diagnostic information superimposed thereon.

An electrophysiology processor, which also may be incorporated within computer system 92, processes the measured electrophysiology information in order to identify one or more surface points that are potential treatment sites. By way of example only, the electrophysiology processor may identify surface points having abnormal impedance as potential targets for tissue ablation in the diagnosis and treatment of cardiac arrhythmia. The electrophysiology processor may be coupled to display 156 such that the one or more identified potential treatment sites, or other indicia of the measured physiological or electrophysiological information, may be presented to the user by superimposition on the graphical representation of the three-dimensional model. For example, the potential treatment sites may be flagged on display 156 with a special icon or coloration. Alternatively, contour lines may be added to the graphical representation to illustrate the physiological and/or electrophysiological data included in the diagnosis map. FIG. 15 illustrates a graphical representation of heart chamber 152 including both flagged potential treatment sites 168 and contour lines 170.

The user may employ a user interface 166, including display 156 and input devices 158, to select one or more of the identified potential treatment sites as target points (also referred to herein as "treatment points"), for example by pointing to and clicking on the treatment site as superimposed on the graphical representation. In order to permit the user to intuitively designate target points, display 156 may be a touchscreen. User interface 166 is preferably coupled to controller 24, and thus to probe 12, such that, upon selecting one or more target points with user interface 166, controller 24 may cause probe 12 to be relocated thereto for further diagnosis (e.g., the collection of additional electrophysiology information at the target site) or treatment (e.g., the delivery of a therapeutic compound or ablative energy to the target site). It is also contemplated that controller 24 may operate to automatically navigate probe 12 to one or more identified potential treatment sites for further diagnosis or treatment without intervention or target point selection by the user (i.e., controller 24 may be responsive directly to the electrophysiology processor).

In use, electrode 154, which is preferably mounted on medical device 12, is inserted within heart chamber 152. (Recall that this term does not embrace embedding electrode 154 in cardiac tissue.) Robotic controller 24 is used to move electrode 154 within heart chamber 152 either randomly, pseudo-randomly, or according to one or more predetermined patterns, and into meaningful proximity with a plurality of surface points on tissue surface 82 of heart chamber 152 in order to measure electrophysiology information thereat.

Assuming a known geometry of heart chamber 152, for example as generated by the surface modeling methodology disclosed herein, electrophysiology information is measured and associated with the pre-existing position information for a plurality of surface points. If the geometry is unknown, the diagnosis mapping and surface modeling processes may be combined such that, as electrode 154 moves within heart chamber 152, both position information and electrophysiology information are measured, thereby simultaneously generating a plurality of location points defining the space occupied by heart chamber 152, at least some of which are surface points, and electrophysiology information for those surface points. The plurality of location points may be processed as described herein or according to another surface construction algorithm to generate the three-dimensional surface model of heart chamber 152. The measured electrophysiology information is associated with the position information for at least some of the plurality of surface points in order to generate the diagnosis map. It is also contemplated that electrophysiology measurements may be taken after generating the plurality of location points, rather than simultaneously therewith, and either before or after applying the surface construction algorithm to generate the surface model.

The diagnosis map can be generated from the resulting plurality of surface diagnostic data points. The plurality of surface diagnostic data points may also be used to generate a three-dimensional surface model of heart chamber 152 including both position and electrophysiology information for the plurality of surface points. The diagnosis map and/or surface model may optionally be stored in a storage medium, either individually or as a composite, or presented as a graphical representation on display 156, either with or without an accompanying three-dimensional model of heart chamber 152.

Once the diagnosis map is generated, it may be used as an intuitive interface for the user to select one or more target points, for example by using an input device 158 to point and click on the graphical representation of the three-dimensional model of heart chamber 152 with the diagnosis map superimposed thereon. Medical device 12 may subsequently be navigated to the target points so selected in order to provide treatment, such as ablation of tissue, or for further diagnosis, such as making additional electrophysiology measurements. It is contemplated that the user selecting the one or more target points may be remote from robotic surgical system 10. For example, an expert physician in one city may access the three-dimensional model of heart chamber 152 via a computer network, such as the Internet, and select the target points, which may then be delivered to robotic surgical system 10 in a second city for execution.

Although several embodiments of this invention have been described above with a certain degree of particularity, those skilled in the art could make numerous alterations to the disclosed embodiments without departing from the spirit or scope of this invention. For example, the robotic surgical system 10 may be modified to incorporate additional servo mechanisms and controllers operating on additional degrees of freedom.

Further, though the contact sensing methodology has been described in connection with a robotically controlled medical device, it could also be implemented in a manually controlled medical device. It should also be understood that, rather than utilizing absolute values in the various contact sensing algorithms described herein, the thresholds or limits may be appropriately adjusted to compensate for negative values of $\Delta P$, for example by taking the opposite of all thresholds or limits and reversing the comparator (i.e., changing < to >) upon detecting that $\Delta P$ is less than zero.

In addition, one of ordinary skill in the art will appreciate that, though the devices and methods disclosed herein have been described in connection with the treatment of atrial fibrillation, and in particular in connection with the creation of lesions of ablated tissue, they may be used to administer other therapies or to perform other diagnostic procedures.

Further, the devices and methods disclosed herein are capable of use both epicardially and endocardially.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of generating a diagnosis map of at least a portion of a heart, comprising the steps of:
   inserting an electrode within a portion of a heart;
   robotically moving the electrode within the portion of the heart;

detecting position information of the electrode, thereby generating a plurality of location points that define a space occupied by the portion of the heart, the plurality of location points including both location points interior to a surface of the heart and location points on the surface of the heart;

measuring electrophysiology information from the surface of the heart as the electrode is robotically moved within the portion of the heart;

distinguishing the location points interior to a surface of the portion of the heart from the location points on the surface of the portion of the heart;

associating the measured electrophysiology information from the surface of the heart with the location point on the surface of the heart at which the measurement was made as a surface diagnostic data point;

storing the surface diagnostic data point; and generating a three-dimensional model of the portion of the heart comprising a plurality of surface diagnostic data points.

2. The method of claim 1, further comprising:

presenting a graphical representation of the three-dimensional model of the portion of the heart;

receiving input that identifies one or more target locations on the graphical representation of the three-dimensional model of the portion of the heart; and robotically moving the electrode to each of the identified target locations.

3. The method of claim 2, further comprising presenting the graphical representation of the three-dimensional model of the portion of the heart with information indicative of the measured electrophysiology information superimposed thereon.

4. The method of claim 2, further comprising treating tissue at each of the identified target locations.

5. The method of claim 4, wherein treating tissue at each of the identified target locations comprises ablating tissue at each of the identified target locations.

6. The method of claim 1, further comprising:

presenting a graphical representation of the three-dimensional model of the portion of the heart;

processing the plurality of surface diagnostic data points to identify one or more surface diagnostic data points that are potential treatment sites; and flagging the one or more identified potential treatment sites on the graphical representation of the three-dimensional model of the portion of the heart.

7. The method of claim 6, further comprising:

receiving input that selects one or more of the identified potential treatment sites on the graphical representation of the three-dimensional model of the portion of the heart; and robotically moving the electrode to at least one selected treatment site.

8. The method according to claim 7, further comprising treating tissue at the at least one selected treatment site.

9. The method according to claim 8, wherein treating tissue at the at least one selected treatment site comprises ablating tissue at the at least one selected treatment site.

10. A system for generating a diagnosis map of at least a portion of a heart, comprising:

a catheter for insertion into an interior region of the heart;

a robotic controller operable to move the catheter within the interior region of the heart;

a positional feedback system operable to detect position information of the catheter as the robotic controller moves the catheter within the interior region of the heart, thereby generating a plurality of location points that define a space occupied by the portion of the heart; and a modeling processor programmed to distinguish those location points that are interior to a surface of the portion of the heart from those location points that are on the surface of the portion of the heart and to define a three-dimensional surface model of the portion of the heart from those location points that are on the surface of the portion of the heart.

11. The system of claim 10, wherein the catheter further comprises a sensor to measure electrophysiological information for at least some of the location points that are on the surface of the portion of the heart, and wherein the modeling processor is further programmed to associate measured electrophysiological information with the location point on the surface of the portion of the heart at which the measurement was made, thereby generating a plurality of surface diagnostic data points.

12. The system of claim 11, further comprising a storage medium for storing the plurality of surface diagnostic data points, and wherein the modeling processor is further programmed to store the plurality of surface diagnostic data points in the storage medium.

13. The system of claim 11, further comprising:

a display device for presenting a graphical representation of the three-dimensional surface model of the portion of the heart; and an electrophysiology processor programmed to process the measured electrophysiological information to identify one or more surface diagnostic data points that are potential treatment sites and to graphically flag the one or more identified potential treatment sites on the graphical representation of the three-dimensional surface model of the portion of the heart.

14. The system of claim 11, further comprising:

a display device for presenting a graphical representation of the three-dimensional surface model of the portion of the heart; and a user interface operable to permit a user to select one or more locations on the graphical representation of the three-dimensional surface model of the portion of the heart as one or more target locations, the user interface being coupled to the robotic controller such that the robotic controller operates to cause the catheter to be relocated to the one or more target locations.

* * * * *